(12) United States Patent
Ikawa et al.

(10) Patent No.: US 6,555,584 B1
(45) Date of Patent: Apr. 29, 2003

(54) ACYLSULFONAMIDE DERIVATIVE

(75) Inventors: Hiroshi Ikawa, Tokyo (JP); Masato Nishimura, Tokyo (JP); Keiji Okada, Tokyo (JP); Takashi Nakamura, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/606,191

(22) Filed: Jun. 29, 2000

(51) Int. Cl.$^7$ .................. A61K 31/18; C07C 311/16
(52) U.S. Cl. ................. 514/603; 564/86; 564/88; 564/90; 564/92
(58) Field of Search .............. 564/92, 86, 88, 564/90; 514/603

(56) References Cited

U.S. PATENT DOCUMENTS 6,235,680 B1 * 5/2001 Ziemer et al. .............. 504/112

FOREIGN PATENT DOCUMENTS

GB  1336983  * 11/1973  ................. 514/603

OTHER PUBLICATIONS

Chemical Abstracts, vol. 131, (6), abst.No. 73368j pub.Aug. 9, 1999 which abstracts Jpn.Kokai Tokkyo Koho, Jp 11 171,856, 38 pages published Jun. 29, 1999.*

* cited by examiner

*Primary Examiner*—Charanjit S. Aulakh
(74) *Attorney, Agent, or Firm*—Oblon, Spivak, McClelland, Maier & Neustadt, P.C.

(57) ABSTRACT

This invention provides a novel acylsulfonamide derivative which can be used as an ACC activity inhibitor effective for the treatment of visceral fat syndrome that becomes the risk-factor of diseases of adult people such as myocardial infarction, cerebral infarction and diabetes.

Particularly, it relates to an acylsulfonamide derivative represented by a general formula 1

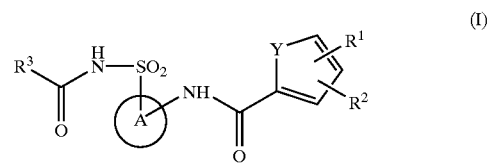

wherein $R^1$ is substituted/unsubstituted $C_2$–$C_{12}$ alkyl or alkoxy group or substituted/unsubstituted $C_2$–$C_{12}$ alkenyl or alkynyl group, $R^2$ is hydrogen atom, hydroxyl group, mercapto group, substituted/unsubstituted $C_1$–$C_6$ alkoxy or alkylthio group, nitro group, halogen atom, trichloromethyl group, trifluoromethyl group or cyano group, $R^3$ is substituted/unsubstituted $C_1$–$C_{20}$ alkyl or alkoxy group, substituted/unsubstituted $C_2$–$C_{20}$ alkenyl or alkynyl group, substituted/unsubstituted aromatic hydrocarbon or aromatic heterocyclic group, substituted amino group, substituted/unsubstituted $C_2$–$C_{20}$ alkenyloxy or alkynyloxy group or $R^4O$— (wherein $R^4$ is substituted/unsubstituted aromatic hydrocarbon or aromatic heterocyclic group), Y is —CH=CH—, —N=CH—, —CH=N—, sulfur or oxygen, and ring A is aromatic hydrocarbon, aromatic heterocyclic ring or cyclic alkyl group.

5 Claims, No Drawings

ACYLSULFONAMIDE DERIVATIVE

FIELD OF THE INVENTION

This invention relates to acylsulfonamide derivatives, more particularly to a novel acylsulfonamide derivative which has the activity to inhibit acetyl-CoA carboxylase (also to be referred to as "ACC" hereinafter).

BACKGROUND ART

It has been revealed in recent years that excess accumulation of neutral fat, particularly triglyceride, in visceral fat tissue is an important risk-factor for various diseases such as hyperlipemia, hypertension, arteriosclerosis, myocardial infarction and glucose tolerance abnormality. That is, it is considered that fatty acid synthesis is activated in the visceral fat tissue, and the fatty acids accelerate insulin resistance when released in the portal vein and are further incorporated into the liver and used as materials of triglyceride which is then released into blood plasma to cause hypertriglyceridemia.

On the other hand, ACC is an enzyme which catalyzes synthesis of malonyl-CoA from acetyl-CoA and is a rate-limiting enzyme in the biosynthesis of long chain fatty acids. Also, it is known that the malonyl-CoA itself synthesized from acetyl-CoA by the action of ACC controls carnitine acyltransferase which is concerned in the consumption of free long chain fatty acids as energy source. In addition, it is considered that activation of ACC is concerned in the activation of fatty acid synthesis in the visceral fat tissue. In consequence, an agent capable of inhibiting the ACC activity inhibits biosynthesis of long chain fatty acids in the living body, while simultaneously accelerating their metabolism, and thereby reduces the amount of long chain fatty acids in the living body and inhibits biosynthesis of triglyceride as a result, so that it has a possibility as a drug for the treatment and prevention of various diseases caused by the accumulation of visceral fat.

SUMMARY OF THE INVENTION

Based on such a viewpoint, the present inventors have conducted intensive studies with the aim of finding an ACC activity inhibitor effective for the treatment of visceral fat syndrome which becomes the risk-factor for diseases of adult people such as myocardial infarction, cerebral infarction and diabetes, and have newly found as a result of the efforts that excellent ACC inhibition activity can be found in acylsulfonamide derivatives represented by a general formula (I) shown in the following. The invention has been accomplished based on this finding. Thus, the invention contemplates providing a novel acylsulfonamide derivative and a medicament, particularly an ACC activity inhibitor, which uses such compound as the active ingredient.

Accordingly, an object of the invention is to provide an acylsulfonamide derivative represented by a general formula 1

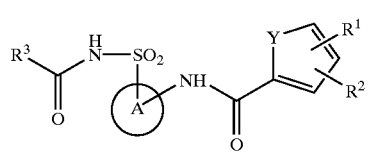

(I)

wherein $R^1$ represents a substituted or unsubstituted $C_1$–$C_{12}$ alkyl group, a substituted or unsubstituted $C_2$–$C_{12}$ alkenyl group, a substituted or unsubstituted $C_2$–$C_{12}$ alkynyl group or a substituted or unsubstituted $C_1$–$C_{12}$ alkoxy group, $R^2$ represents a hydrogen atom, a hydroxyl group, a mercapto group, a substituted or unsubstituted $C_1$–$C_6$ alkoxy group, a substituted or unsubstituted $C_1$–$C_6$ alkylthio group, a nitro group, a halogen atom, a trichloromethyl group, a trifluoromethyl group or a cyano group, $R^3$ represents a substituted or unsubstituted $C_1$–$C_{20}$ alkyl group, a substituted or unsubstituted $C_2$–$C_{20}$ alkenyl group, a substituted or unsubstituted $C_2$–$C_{20}$ alkynyl group, a substituted or unsubstituted aromatic hydrocarbon group, a substituted or unsubstituted aromatic heterocyclic group, a substituted amino group, a substituted or unsubstituted $C_1$–$C_{20}$ alkoxy group, a substituted or unsubstituted $C_2$–$C_{20}$ alkenyloxy group, a substituted or unsubstituted $C_2$–$C_{20}$ alkynyloxy group or a group represented by $R^4O$— (wherein $R^4$ represents a substituted or unsubstituted aromatic hydrocarbon group or a substituted or unsubstituted aromatic heterocyclic group), Y is a group represented by —CH=CH—, —N=CH— or —CH=N—, sulfur atom or oxygen atom, and ring A represents a substituted or unsubstituted aromatic hydrocarbon group, a substituted or unsubstituted aromatic heterocyclic group or a substituted or unsubstituted cyclic alkyl group.

Other objects and advantages of the invention will be made apparent as the description progresses.

DETAILED DESCRIPTION OF THE INVENTION

The acylsulfonamide derivatives represented by the general formula (I), to be provided by the invention, are novel compounds which have not been known to date, and the presence of ACC activity inhibition action in these compounds has not been known either. However, as is evident from the results of pharmacological tests which will be described later, it was revealed that these compounds have excellent ACC activity inhibition action. In consequence, these compounds are markedly useful particularly as the ACC activity inhibitor effective for the treatment of visceral fat syndrome that becomes the risk-factor for diseases of adult people such as myocardial infarction, cerebral infarction and diabetes. Thus, as its another embodiment, the invention also provides a medicament which uses the acylsulfonamide derivative represented by the general formula (I) as an active ingredient.

The acylsulfonamide derivatives to be provided by the invention are described in detail in the following. The term "$C_1$–$C_{12}$ alkyl group" as used herein means any one of straight, branched and cyclic groups, and its examples include methyl, ethyl, n-propyl, 1-methylethyl, cyclopropyl, n-butyl, 2-methylpropyl, 1-methylpropyl, 1,1-dimethylethyl, cyclobutyl, n-pentyl, 1-methylbutyl, 2-methylbutyl, 3-methylbutyl, cyclopentyl, 2,2-dimethylpropyl, n-hexyl, 1-methylpentyl, 2-methylpentyl, 4-methylpentyl, 1-ethylbutyl, 2-ethylbutyl, 3,3-dimethylbutyl, cyclohexyl, n-heptyl, 1-methylhexyl, 2-methylhexyl, 5-methylhexyl, 4,4-dimethylpentyl, 1-propylbutyl, 2-ethylpentyl, cyclohexylmethyl, 1,1-diethylpropyl, cycoheptyl, n-octyl, 1-methylheptyl, 6-methylheptyl, 1-ethylhexyl, 2-ethylhexyl, 2-cyclohexylethyl, 5,5-dimethylhexyl, cyclooctyl, n-nonyl, 1-methyloctyl, 7-methyloctyl, 6,6-dimethylheptyl, n-decyl, 1-methylnonyl, 8-methylnonyl, 7,7-dimethyloctyl, n-undecyl, 1-methyldecyl, 9-methyldecyl, 8,8-dimethylnonyl, n-dodecyl, 1-methylundecyl, 10-methylundecyl, 5-methylundecyl and 9,9-dimethyldecyl. Also, these alkyl groups may further have various substituents. Examples of such substituents include halogen atoms such as chlorine, bromine, iodine and fluorine, nitro group, amino group, cyano group, hydroxyl group, alkoxy group, thiol group, trichloromethyl group, trifluoromethyl group, aromatic hydrocarbon groups such as phenyl group and naphthyl group, and aromatic heterocyclic groups such as thienyl, furyl and pyridyl. In addition, these aromatic hydrocarbon groups and aromatic heterocyclic groups may also have substituents such as halogen atom, alkyl group, alkoxy group, nitro group, amino group, cyano group, hydroxyl group and thiol group.

The term "$C_1$–$C_{20}$ alkyl group" as used herein means any one of straight, branched and cyclic groups, and its examples include dodecyl, tetradecyl, pentadecyl, hexadecyl, heptadecyl, octadecyl, nonadecyl and eicosyl, in addition to those which are exemplified regarding the "$C_1$–$C_{12}$ alkyl group". These alkyl groups may further have various substituents. The same substituents of the "$C_1$–$C_{20}$ alkyl group" can be exemplified as such substituents.

The term "substituted or unsubstituted aromatic hydrocarbon group" means an aromatic hydrocarbon group which is monocyclic or polycyclic and may have one or more of various substituents on the ring, and its examples include phenyl, methylphenyl, dimethylphenyl, methoxyphenyl, dimethoxyphenyl, nitrophenyl, dinitrophenyl, chlorophenyl, dichlorophenyl, bromophenyl, dibromophenyl, iodophenyl, fluorophenyl, trifluoromethylphenyl, aminophenyl, hydroxyphenyl, mercaptophenyl, α-naphthyl and β-naphthyl.

The term "substituted or unsubstituted aromatic heterocyclic group" means a five or six-membered ring group containing at least one hetero atom such as nitrogen atom, sulfur atom or oxygen atom as a ring-constituting atom, which may be considered with benzene ring(s) and may have one or more of various substituents on the ring, and its examples include pyridyl, furyl, thienyl, indolyl, quinolyl, isoquinolyl, benzofuranyl, benzothienyl, imidazolyl, benzimidazolyl, thiazolyl, oxazolyl, pyrazolyl, pyrimidyl, pyrazinyl, isoxazolyl, isoindolyl and pyrrolyl.

The term "$C_2$–$C_{12}$ alkenyl group" means a linear or branched group, and its examples include 1-methyl-1-propenyl, 1-methyl-2-propenyl, 2-methyl-2-propenyl, ethenyl, 1-methylethenyl, 1-propenyl, 2-propenyl, 1-butenyl, 2-butenyl, 2-pentenyl, 1-pentenyl, 3-methylbutenyl, 1,3-butanedienyl, 1-hexenyl, 2-hexenyl, 3,3-dimethyl-1-butenyl, 4,4-dimethyl-1-pentenyl, 1,3-pentanedienyl, 1,3-hexanedienyl, 2-cyclohexylethenyl, octenyl, nonenyl, decenyl, undecenyl and dodecenyl. These alkenyl groups may further have various substituents. The same substituents of the "$C_1$–$C_{12}$ alkyl group" can be exemplified as such substituents.

The term "$C_2$–$C_{20}$ alkenyl group" means any one of linear, branched or cyclic groups, and its examples include tridecenyl, tridecadienyl, tetradecenyl, tetradecadienyl, pentadecenyl, pentadecadienyl, pentadecatrienyl, hexadecenyl, hexadecadienyl, hexadecatrienyl, heptadecenyl, heptadecadienyl, heptadecatrienyl, octadecenyl, octadecadienyl, octadecatrienyl, nonadecenyl, nonadecadienyl, nonadecatrienyl, eicosenyl, eicosadienyl and eicosatrienyl, in addition to those which are exemplified regarding the "$C_2$–$C_{12}$ alkyl group". These alkenyl groups may further have various substituents. The same substituents of the "$C_1$–$C_{12}$ alkyl group" can be exemplified as such substituents.

The term "$C_2$–$C_{12}$ alkynyl group" means a linear or branched group, and its examples include 1-propynyl, 2-propynyl, 1-methyl-2-propynyl, 1-ethyl-2-propynyl, ethynyl, 1-butynyl, 2-butynyl, 1,3-butadiynyl, 1-pentynyl, 2-pentynyl, 1,3-pentadiynyl, 1-hexynyl, 2-hexynyl and 1,3-hexadiynyl. These groups may further have various substituents. The same substituents of the "$C_1$–$C_{12}$ alkyl group" can be exemplified as such substituents.

The term "$C_2$–$C_{20}$ alkynyl group" means any one of linear, branched and cyclic groups, and its examples include tridecynyl, tridecadiynyl, tetradecynyl, tetradecadiylyl, pentadecynyl, pentadecadiynyl, pentadecatriynyl, hexadecynyl, headecadiynyl, hexadecatriynyl, heptadecynyl, heptadecadiynyl, heptadecatriynyl, octadecynyl, octadecadiynyl, octadecatriynyl, nonadecynyl, nonadecadiynyl, nonadecatriynyl, eicosynyl, eicosadiynyl and eicosatriynyl, in addition to those which are exemplified regarding the "$C_2$–$C_{12}$ alkyl group". These alkenyl groups may further have various substituents. The same substituents of the "$C_1$–$C_{12}$ alkyl group" can be exemplified as such substituents.

The term "substituted amino group" means a group in which its nitrogen atom is substituted by one or two of a substituted or unsubstituted $C_1$–$C_{20}$ alkyl group, a substituted or unsubstituted $C_2$–$C_{20}$ alkenyl group, a substituted or unsubstituted $C_2$–$C_{20}$ alkynyl group, a substituted or unsubstituted aromatic hydrocarbon group and a substituted or unsubstituted aromatic heterocyclic group, and the alkyl group together with the binding nitrogen atom may form a five- to seven-membered saturated heterocyclic ring which may contain nitrogen atom, oxygen atom or sulfur atom. Examples of this substituted amino group include methylamino, ethylamino, propylamino, butylamino, pentylamino, hexylamino, dimethyamino, diethylamino, dipropylamino, 2-propenylamino, 2-butenylamino, 3-butenylamino, 1-pyrrolidinyl, piperidino, 1-piperazinyl, morpholino, thiomorpholino, perhydroazepinyl, phenylamino, naphthylamino, pyridylamino, furylamino and thienylamino.

The term "$C_1$–$C_{12}$ alkoxy group" means an alkyl-substituted oxy group wherein the alkyl group is as described in the foregoing, and its examples include methoxy, ethoxy, n-propoxy, 1-methylethoxy, n-butoxy, 2-methylpropoxy, 1-methylpropoxy, 2-methyl-2-propoxy, n-pentyloxy, 3-methylbutoxy, n-hexyloxy, 4-methylpentoxy, n-pentyloxy, n-octyloxy, n-nonyloxy, n-decyloxy and n-undecyloxy. These alkyl groups may further have various substituents. The same substituents of the "$C_1$–$C_{22}$ alkyl group" can be exemplified as such substituents.

The term "$C_1$–$C_{20}$ alkoxy groups" means any one of linear, branched and cyclic groups, and its examples include tridecyloxy, tetradecyloxy, pentadecyloxy, hexadecyloxy, heptadecyloxy, octadecyloxy, nonadecyloxy and eicosyloxy, in addition to those which are exemplified regarding the "$C_1$–$C_{12}$ alkoxy group". These alkoxy groups may further have various substituents. The same substituents of the "$C_1$–$C_{12}$ alkyl group" can be exemplified as such substituents.

The term "$C_1$–$C_6$ alkylthio group" means an alkyl-substituted thio group wherein the alkyl group is as described in the foregoing, and its examples include methylthio, ethylthio, n-propylthio, 1-methylethylthio, n-butylthio, 2-methylpropylthio, 1-methylpropylthio, 2-methyl-2-propylthio, n-pentylthio, 3-methylbutylthio, n-hexylthio and 4-methylpentylthio. These alkylthio groups may further have various substituents. The same substituents of the "$C_1$–$C_{12}$ alkyl group" can be exemplified as such substituents.

In the acylsulfonamide derivatives represented by the general formula (I), which are provided by the invention, the ring shown by A is the aromatic hydrocarbon group or aromatic heterocyclic group described in the foregoing. As the substitution mode of these groups, it is desirable that the acylsulfonamide side chain and amide side chain have their substitution sites at the 1,2-position, or at the 1,1-position when A is a cyclic alkyl group.

Also, in the acylsulfonamide derivatives represented by the general formula (I), it is desirable that $R^1$ is a $C_1$–$C_4$ alkyl group having a substitution or unsubstituted aromatic hydrocarbon group or a substituted or unsubstituted aromatic heterocyclic group as a substituent, a $C_2$–$C_4$ alkenyl group having a substituted or unsubstituted aromatic hydrocarbon group or a substituted or unsubstituted aromatic heterocyclic group as a substituent, a $C_2$–$C_4$ alkynyl group having a substituted or unsubstituted aromatic hydrocarbon group or a substituted or unsubstituted aromatic heterocyclic group as a substituent or a $C_1$–$C_4$ alkoxy group having a substituted or unsubstituted aromatic hydrocarbon group or a substituted or unsubstituted aromatic heterocyclic group as a substituent.

Also, in the acylsulfonamide derivatives represented by the general formula (I), it is desirable that $R^1$ is an unsubstituted $C_5$–$C_{22}$ alkyl group, an unsubstituted $C_5$–$C_{12}$ alkenyl group, an unsubstituted $C_5$–$C_{22}$ alkynyl group or an unsubstituted $C_5$–$C_{22}$ alkoxy group.

The following compounds can be exemplified as the acylsulfonamide derivatives of the invention.

N-[2-(3-Benzyloxybenzamido)benzenesulfonyl] benzamide;

N-[2-(3-benzyloxybenzamido)benzenesulfonyl] acetamide;

N-[2-(3-benzyloxybenzamido)benzenesulfonyl]-4-benzyloxybenzamide;

N-[2-(3-benzyloxybenzamido)benzenesulfonyl]-3-benzyloxybenzamide;

N-[2-(3-benzyloxybenzamido)benzenesulfonyl]-2-benzyloxybenzamide;

N-[2-(4-benzyloxybenzamido)benzenesulfonyl]-4-trifluoromethylbenzamide;

N-[2-(3-benzyloxybenzamido)benzenesulfonyl]-4-trifluoromethylbenzamide;

N-[2-(3-benzyloxybenzamido)benzenesulfonyl]-4-methoxybenzamide;

N-[2-(3-benzyloxybenzamido)benzenesulfonyl]-4-nitrobenzamide;

N-[2-(4-phenylethynylbenzamido)benzenesulfonyl]-3-benzyloxybenzamide;

N-[2-[4-(2-phenyl-(E)-ethenyl)benzamido] benzenesulfonyl]-4-trifluoromethylbenzamide;

N-[2-(4-phenylethynylbenzamido)benzenesulfonyl]-3-benzyloxybenzamide;

N-[2-(4-phenylethynylbenzamido)benzenesulfonyl]-4-trifluoromethylbenzamide;

N-[2-(4-phenylethynylbenzamido)benzenesulfonyl]-4-nitrobenzamide;

N-[2-(3-benzyloxybenzamido)benzenesulfonyl]-3,4-difluorobenzamide;

N-[2-(3-benzyloxybenzamido)benzenesulfonyl]-3,4,5-trifluorobenzamide;

N-[2-(3-benzyloxybenzamido)benzenesulfonyl] hexanamide;

N-[2-(3-benzyloxybenzamido)benzenesulfonyl] decanamide;

N-[2-(3-benzyloxybenzamido)benzenesulfonyl] dodecanamide;

N-[2-(3-benzyloxybenzamido)benzenesulfonyl] cyclohexanamide;

N-[2-(3-benzyloxybenzamido)benzenesulfonyl]-3-benzyloxy-5-nitrobenzamide;

N-[2-(3-benzyloxybenzamido)benzenesulfonyl]-3-benzyloxy-5-trifluoromethylbenzamide;

N-[2-(3-benzyloxybenzamido)benzenesulfonyl]-3-benzyloxy-5-chlorobenzamide;

N-[2-(3-benzyloxybenzamido)benzenesulfonyl]-3-benzyloxy-5-fluorobenzamide;

N-[2-(3-benzyloxybenzamido)benzenesulfonyl]-3-benzyloxy-4-nitrobenzamide;

N-[2-(3-benzyloxybenzamido)benzenesulfonyl]-3-benzyloxy-4-trifluoromethylbenzamide;

N-[2-(3-benzyloxybenzamido)benzenesulfonyl]-3-benzyloxy-4-chlorobenzamide;

N-[2-(3-benzyloxybenzamido)benzenesulfonyl]-3-benzyloxy-4-fluorobenzamide;

N-[2-(4-phenylethynylbenzamido)pyridinesulfonyl]-4-nitrobenzamide;

N-[2-(4-phenylethynylbenzamido)pyrazinesulfonyl]-4-nitrobenzamide;

N-[2-(3-naphthyloxybenzamido)benzenesulfonyl] butanamide;

N-[2-(3-naphthylmethoxybenzamido)benzenesulfonyl] butanamide;

N-[2-(3-furyloxybenzamido)benzenesulfonyl] butanamide;

N-[2-(3-furylmethoxybenzamido)benzenesulfonyl] butanamide;

N-[2-(3-thienyloxybenzamido)benzenesulfonyl] butanamide;

N-[2-(3-thienylmethoxybenzamido)benzenesulfonyl] butanamide;

N-[2-(3-pyridyloxybenzamido)benzenesulfonyl] butanamide;

N-[2-(3-pyridylmethoxybenzamido)benzenesulfonyl] butanamide;

N-[2-(3-phenyloxybenzamido)benzenesulfonyl] butanamide;

N-[2-(3-benzyloxybenzamido)benzenesulfonyl] butanamide;

N-[2-(3-benzyloxybenzamido)benzenesulfonyl] pentanamide;

N-[2-(3-benzyloxybenzamido)benzenesulfonyl] heptanamide;

N-[2-(3-benzyloxybenzamido)benzenesulfonyl] octanamide;

N-[2-(3-benzyloxybenzamido)benzenesulfonyl] nonanamide;

N-[2-(3-benzyloxybenzamido)benzenesulfonyl] decanamide;

N-[2-(3-benzyloxybenzamido)benzenesulfonyl] dodecanamide;

N-[2-(3-benzyloxybenzamido)benzenesulfonyl] tetradecanamide;

N-[2-(4-benzyloxybenzamido)benzenesulfonyl] butanamide;

N-[2-(4-benzyloxybenzamido)benzenesulfonyl] pentanamide;
N-[2-(4-benzyloxybenzamido)benzenesulfonyl] heptanamide;
N-[2-(4-benzyloxybenzamido)benzenesulfonyl] octanamide;
N-[2-(4-benzyloxybenzamido)benzenesulfonyl] nonanamide;
N-[2-(4-benzyloxybenzamido)benzenesulfonyl] decanamide;
N-[2-(4-benzyloxybenzamido)benzenesulfonyl] dodecanamide;
N-[2-(4-benzyloxybenzamido)benzenesulfonyl] tetradecanamide;
N-[2-(3-benzyloxybenzamido)benzenesulfonyl] hexadecanamide;
N-[2-(3-benzyloxybenzamido)benzenesulfonyl] octadecanamide;
N-[2-(3-benzyloxybenzamido)benzenesulfonyl] pentafluorobenzamide;
N-[2-(3-benzyloxybenzamido)benzenesulfonyl] eicosanamide;
N-[2-(3-benzyloxybenzamido)benzenesulfonyl]-2,4-difluorobenzamide;
N-[2-[3-(4-t-butylbenzyloxy)benzamido] benzenesulfonyl]pivalamide;
N-[2-[3-(4-t-butylbenzyloxy)benzamido] benzenesulfonyl]cinnamamide;
N-[2-(3-benzyloxybenzamido)benzenesulfonyl] oleinamide;
N-[2-(3-benzyloxybenzamido)benzenesulfonyl] linolamide;
N-[2-(3-benzyloxy-4-nitrobenzamido)benzenesulfonyl] decanamide;
N-[2-(4-chloro-3-benzyloxybenzamido)benzenesulfonyl] decanamide;
N-[2-(3-benzyloxy-4-hydroxybenzamido) benzenesulfonyl]decanamide;
N-[2-(3-benzyloxy-4-cyanobenzamido)benzenesulfonyl] decanamide;
N-[2-(3-benzyloxy-4-methoxybenzamido) benzenesulfonyl]decanamide;
N-[2-[3-(4-chlorobenzyloxy)benzamido] benzenesulfonyl]acetamide;
N-[2-[3-(4-chlorobenzyloxy)benzamido] benzenesulfonyl]hexanamide;
N-[2-[3-(4-chlorobenzyloxy)benzamido] benzenesulfonyl]decanamide;
N-[2-[3-(4-nitrobenzyloxy)benzamido]benzenesulfonyl] acetamide;
N-[2-[3-(4-nitrobenzyloxy)benzamido]benzenesulfonyl] hexanamide;
N-[2-[3-(4-nitrobenzyloxy)benzamido]benzenesulfonyl] decanamide;
N-[2-[3-(4-methoxybenzyloxy)benzamido] benzenesulfonyl]acetamide;
N-[2-[3-(4-methoxybenzyloxy)benzamido] benzenesulfonyl]hexanamide;
N-[2-[3-(4-methoxybenzyloxy)benzamido] benzenesulfonyl]decanamide;
N-[2-(3-cyclohexylmethoxybenzamido)benzenesulfonyl] acetamide;
N-[2-(3-cyclohexylmethoxybenzamido)benzenesulfonyl] hexanamide;
N-[2-(3-cyclohexylmethoxybenzamido)benzenesulfonyl] decanamide;
N-[2-[3-(4-t-butylbenzyloxy)benzamido] benzenesulfonyl]acetamide;
N-[2-[3-(4-t-butylbenzyloxy)benzamido] benzenesulfonyl]hexanamide;
N-[2-[3-(4-t-butylbenzyloxy)benzamido] benzenesulfonyl]decanamide;
N-[2-[3-(4-trifluoromethylbenzyloxy)benzamido] benzenesulfonyl]acetamide;
N-[2-[3-(4-trifluoromethylbenzyloxy)benzamido] benzenesulfonyl]hexanamide;
N-[2-[3-(4-trifluoromethylbenzyloxy)benzamido] benzenesulfonyl]decanamide;
N-[2-(3-heptyloxybenzamido)benzenesulfonyl] acetamide;
N-[2-(3-octyloxybenzamido)benzenesulfonyl]acetamide;
N-[2-(3-decyloxybenzamido)benzenesulfonyl]acetamide;
N-[2-(3-heptyloxybenzamido)benzenesulfonyl] hexanamide;
N-[2-(3-heptyloxybenzamido)benzenesulfonyl] decanamide;
N-[2-(4-phenylethynylbenzamido)benzenesulfonyl] acetamide;
N-[2-[4-(1-hexynyl)benzamido]benzenesulfonyl] acetamide;
N-[2-[4-(1-hexynyl)benzamido]benzenesulfonyl] hexanamide;
N-[2-[4-(1-octynyl)benzamido]benzenesulfonyl] acetamide;
N-[2-[4-(1-octynyl)benzamido]benzenesulfonyl] hexanamide;
N-[2-[4-(3,3-dimethylbutan-1-yl)benzamido] benzenesulfonyl]acetamide;
N-[2-[4-(3,3-dimethylbutan-1-yl)benzamido] benzenesulfonyl]hexanamide;
N-[2-[4-(1-hexenyl)benzamido]benzenesulfonyl] acetamide;
N-[2-[4-(1-hexenyl)benzamido]benzenesulfonyl] hexanamide;
N-[2-[4-(1-octenyl)benzamido]benzenesulfonyl] acetamide;
N-[2-[4-(1-octenyl)benzamido]benzenesulfonyl] hexanamide;
N-[2-[4-(3,3-dimethylbutan-1-enyl)benzamido] benzenesulfonyl]acetamide;
N-[2-[4-(3,3-dimethylbutan-1-enyl)benzamido] benzenesulfonyl]hexanamide;
N-[2-(4-phenylethynylbenzamido)benzenesulfonyl] hexamamide;
N-[2-(4-phenylethynylbenzamido)benzenesulfonyl] decanamide;
N-[2-(4-phenylethynylbenzamido)benzenesulfonyl] pivalamide;
3-methyl-N-[2-(4-phenylethynylbenzamido) benzenesulfonyl]-2-butenamide;
trans-N-[2-(4-phenylethynylbenzamido) benzenesulfonyl]-2,4-hexadienamide;
trans-N-[2-(4-phenylethynylbenzamido) benzenesulfonyl]-3-hexenamide;

3-benzyloxy-N-[2-[(phenyloxycarbonylamino)sulfonyl]
phenyl]benzamide;
3-benzyloxy-N-[2-[[(butylamino)carbonylamino]
sulfonyl]phenyl]benzamide; and
3-benzyloxy-N-[2-[[(octylamino)carbonylamino]
sulfonyl]phenyl]benzamide.

The acylsulfonamide derivatives of the invention can be produced in accordance, for example, with the following method. This production method can be summarized by the following chemical formulae.

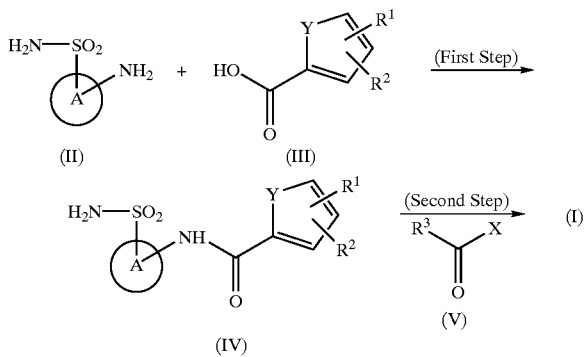

In the above formulae, $R^1$, $R^2$, $R^3$, Y and ring A are as defined in the foregoing, and X is a halogen atom such as chlorine or bromine, succinimido group or imidazolyl group.

(First step) In this step, a sulfonamide compound represented by the formula (IV) is produced by carrying out condensation reaction of an aminosulfonamide compound represented by the formula (II) with a carboxylic acid represented by the formula (III). This step includes a method in which a condensing agent such as carbonyldiimidazole, dicyclohexylcarbodiimide or 1-ethyl-3-(3-dimethylaminopropyl)carbodiimide hydrochloride is used, a method in which the carboxylic acid represented by the formula (III) is converted into a corresponding acid halide using a halogenation agent such as thionyl chloride or phosphorus pentachloride and then condensed in the presence of an appropriate base and a method in which the carboxylic acid represented by the formula (III) is converted into an acid anhyhdride using p-toluenesulfonic acid chloride, ethyl chlorocarbonate or pivaloyl chloride and then condensed in the presence of an appropriate base.

In this reaction, it is desirable to use the aminosulfonamide compound represented by the formula (II) and the carboxylic acid represented by the formula (III) in almost equimolar amounts. The reaction temperature and reaction period are not generally limited due, for example, to the kinds of compounds, but the compound of interest can be obtained with a high yield by carrying out the reaction at a temperature of from about 0° C. to about boiling point of the solvent to be used for a period of approximately from 0.1 to 25 hours. Regarding amount of the condensing agent to be used, it is desirable to add the agent in an amount of about 1.2 equivalents based on the carboxylic acid represented by the formula (III).

Organic bases and inorganic bases can be cited as examples of the base to be used, which include alkali metal hydrides such as sodium hydride and potassium hydride; alkali metal hydroxides such as sodium hydroxide and potassium hydroxide; alkali metal carbonates such as sodium carbonate and potassium carbonate; alkali metal bicarbonates such as sodium bicarbonate and potassium bicarbonate; alkali metal alkoxides such as sodium methoxide, sodium ethoxide, potassium methoxide and potassium tert-butoxide; trialkylamines such as trimethylamine and triethylamine; and pyridines such as pyridine, dimethylaminopyridine, picoline and lutidine. It is desirable to use the base in an amount of from 1 to 10 equivalents based on the carboxylic acid compound.

In this step, the reaction can be carried out in an inert solvent, and examples of such a solvent include ethers such as diethyl ether, tetrahydrofuran and dioxane; aromatic hydrocarbons such as benzene, toluene and xylene; hydrocarbons such as cyclopentane and cyclohexane; halogenated hydrocarbons such as dichloromethane, dichloroethane, trichloroethane and chloroform; nitriles such as acetonitrile and propionitrile; esters such as ethyl acetate; and N,N-dimethylformamide and dimethyl sulfoxide, or their mixtures with water.

(Second step) In this step, an acylsulfonamide compound represented by the formula (I) is produced by allowing a sulfonamide compound represented by the formula (IV) to react with an acyl compound represented by the formula (V) in the presence of a base. In the acyl compound of formula (V) to be used in this step X, is a halogen atom such as chlorine or bromine, succinoimido group or imidazolyl group. Regarding the base to be used, the same base used in the first step can be used, and it is desirable to use it in an amount of from 1 to 10 equivalents based on the carboxylic acid compound. In this reaction, it is desirable to use the sulfonamide compound represented by the formula (IV) and the acyl compound represented by the formula (V) in almost equimolar amounts. The reaction temperature and reaction period are not generally limited due, for example, to the kinds of compounds, but the compound of interest can be obtained with a high yield by carrying out the reaction at a temperature of from about 0° C. to about boiling point of the solvent to be used for a period of approximately from 0.1 to 25 hours. The reaction can be carried out in an inert solvent. The same solvent used in the first step can be exemplified as this inert solvent.

By optionally combining these reactions, the acylsulfonamide derivative of interest represented by the general formula (I) can be obtained, and it can be isolated and purified as occasion demands by subjecting the reaction solution to generally used purification means such as filtration, decantation, extraction, washing, solvent evaporation, column or thin layer chromatography, recrystallization and distillation.

When the acylsulfonamide derivative of the invention represented by the formula (I) is administered to human as a medicament, it is desirable to administer its effective amount, e.g., generally from 5 to 30 mg per day, by oral administration by dividing the daily dose into 1 to 3 doses per day, though it varies depending on various conditions such as the age of each patient and symptoms of the disease to be treated. The medicament of the invention can be made into various dosage forms, e.g., oral administration preparations such as tablets, capsules, granules, powders, troches and solutions. These preparations can be obtained by generally known methods. For example, tablets, capsules, granules, powders or troches can be produced by formulating the compound of general formula (I) of the invention in optional combination, for example, with fillers such as starch, mannitol and lactose; binders such as carboxymethylcellulose sodium and hydroxypropylcellulose; disintegrators such as crystalline cellulose and carboxymethylcellu lose; lubricants such as talk and magnesium stearate; and fluidity improving agents such as soft silicic anhydride. Also, the medicament of the invention can be used as injections. Regarding their preparation method, the compound may be dispersed or solubilized in advance in an aqueous carrier such as physiological saline using a surface active agent or a dispersing agent, or made into a crystalline or freeze-dried preparation for injection use which can be dispersed or solubilized prior to its use. A pH adjusting agent and a stabilizing agent may be added to the aqueous carrier as optional components. The dose and the route of administration of such injections are not particularly limited, and a safe and necessary amount can be administered in one portion or continuously by intravenous, intraarterial, subcutaneous or intraperitoneal administration, in response to the condition of each disease and characteristics of each patient.

The following describes the invention further in detail with reference to Examples and Pharmacological Test Examples, but the invention is not limited to the following descriptions.

Reference Example 1

3-Benzyloxy-N-(2-sulfamoylphenyl)benzamide

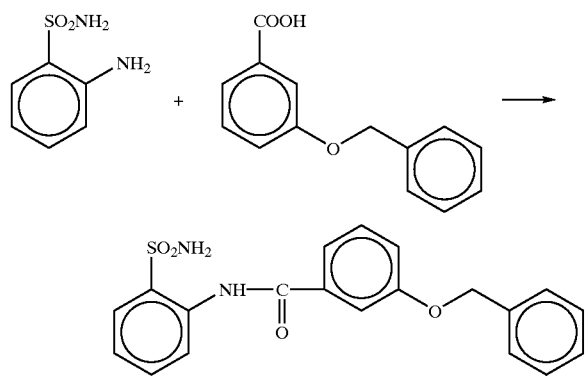

A benzene (40 ml) solution containing 2 g (8.8 mol) of 3-benzyloxybenzoic acid and 8 ml of thionyl chloride was heated under reflux for 2 hours and then the solvent was evaporated. A dioxane (10 ml) solution of the resulting residue was added dropwise to a water-dioxane 1:1 (20 ml) solution containing 1.5 g (8.8 mol) of 2-aminobenzenesulfonamide and 1.62 g (19 mol) of sodium bicarbonate, and the mixture was stirred at room temperature for 1 hour. After completion of the reaction, dioxane was evaporated, the resulting residue was acidified by adding 1 N HCl under ice-cooling and extracted with ethyl acetate. The extract was washed with water and saturated brine and dried over anhydrous sodium sulfate, and then the solvent was evaporated under a reduced pressure. By recrystallizing the resulting residue from acetonitrile 2.0 g (yield: 60%) of the title compound was obtained.

NMR (CDCl$_3$) δ: 4.86 (2H, s), 5.15 (2H, s), 7.18 (1H, dd, J=8 Hz, 1 Hz), 7.26 (1H, ddd, J=8 Hz, 8 Hz, 2 Hz), 7.25–7.48 (6H, m), 7.59 (1H, dd, J=1 Hz, 1 Hz), 7.63 (1H, dd, J=8 Hz, 8 Hz), 7.97 (1H, dd, J=8 Hz, 2 Hz), 8.56 (1H, d, J=8 Hz), 10.03 (1H, s)

IR (ν, cm$^{-1}$, KBr): 1662, 1332, 1151

EI-MS (m/z, %): 382 (M$^+$, 18), 302 (6), 211 (15), 19 (100)

Melting point: 181–182° C.

Example 1

N-[2-(3-Benzyloxybenzamido)benzenesulfonyl]-3-benzyloxybenzamide

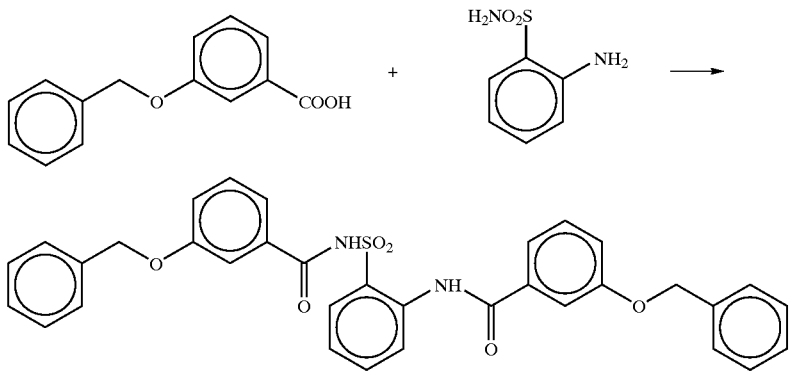

A benzene (10 ml) solution containing 600 mg (2.3 mmol) of 3-benzyloxybenzoic acid and 1.5 ml of thionyl chloride was heated under reflux for 2 hours and then the solvent was evaporated. A dioxane (10 ml) solution of the resulting residue was added dropwise to a water-dioxane 1:1 (10 ml) solution containing 248 mg (1.44 mmol) of 2-aminobenzenesulfonamide and 726 mg (5.2 mmol) of potassium carbonate, and the mixture was stirred at room temperature for 3 hours. After completion of the reaction, dioxane was evaporated, the resulting residue was acidified by adding 1 N HCl under ice-cooling and extracted with ethyl acetate. The extract was washed with water and saturated brine and dried over anhydrous sodium sulfate, and then the solvent was evaporated under a reduced pressure. By recrystallizing the resulting residue from acetonitrile, 200 mg (yield: 90%) of the title compound was obtained.

NMR (CDCl$_3$) δ: 5.01 (2H, s), 5.13 (2H, s), 7.13–7.50 (17H, m), 7.63–7.78 (3H, m), 8.02 (1H, dd, J=8 Hz, 2 Hz), 8.78 (1H, d, J=8 Hz), 8.87 (1H, br-s), 10.59 (1H, s)

IR (ν, cm$^{-1}$, KBr): 1693, 1585, 1340, 1278, 1159, 1029

EI-MS (m/z, %): 592 (M$^+$, 24), 368 (7), 300 (11), 212 (7), 211 (41), 181 (10), 121 (10)

Melting point: 172–173° C.

Example 2

N-[2-(3-Benzyloxybenzamido)benzenesulfonyl]benzamide

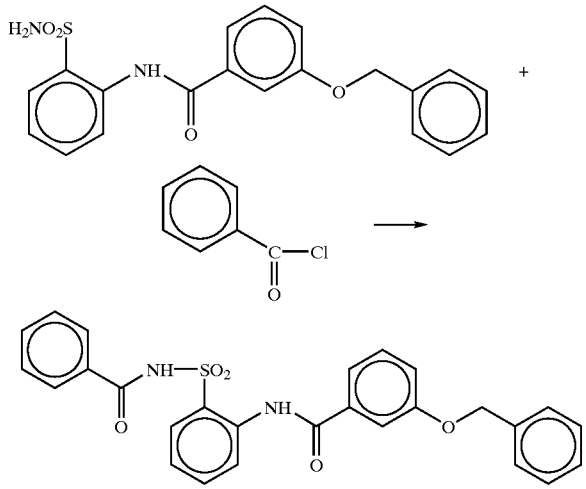

In a stream of nitrogen and under ice-cooling, 88 mg (0.78 mmol) of potassium t-butoxide was added to an anhydrous tetrahydrofuran (10 ml) solution containing 300 mg (0.78 mmol) of 2-(3-benzyloxybenzamido)benzenesulfonamide produced in Reference Example 1, and the mixture was stirred for 1 hour. This solution was mixed with 111 mg (0.78 mmol) of benzoyl chloride and stirred at room temperature for 3 hours. After completion of the reaction, this was neutralized by adding an ammonium chloride aqueous solution and then the solvent was evaporated. The resulting residue was extracted with ethyl acetate, washed with water and saturated brine and dried over anhydrous sodium sulfate, and then the solvent was evaporated under a reduced pressure. The resulting residue was purified by a silica gel column chromatography to obtain 247 mg (yield: 65%) of the title compound.

NMR (CDCl$_3$) δ: 5.15 (2H, s), 7.17–7.46 (10H, m), 7.59 (1H, dd, J=8 Hz, 8 Hz), 7.66–7.76 (5H, m), 8.03 (1H, d, J=8 Hz), 8.78 (1H, d, J=8 Hz), 8.81 (1H, s), 10.61 (1H, s)

IR (ν, cm$^{-1}$, KBr): 3396, 3255, 1687, 1675, 1578, 1529, 1440, 1340, 1303, 1162, 707

EI-MS (m/z, %): 486 (M$^+$, 10), 365 (6), 303 (8), 302 (5), 212 (4), 211 (16)

Melting point: 201–202° C.

Example 3

N-[2-(3-Benzyloxybenzamido)benzenesulfonyl]acetamide

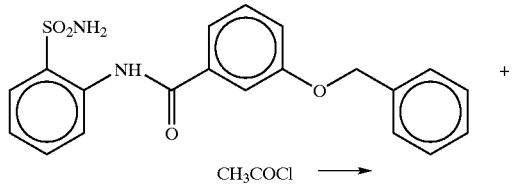

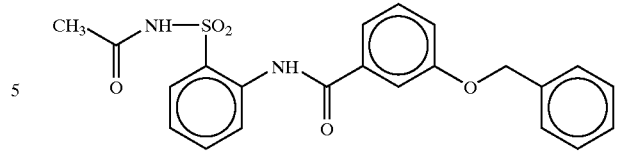

In a stream of nitrogen and under ice-cooling, 162 mg (1.44 mmol) of potassium t-butoxide was added to an anhydrous tetrahydrofuran (10 ml) solution containing 400 mg (1.04 mmol) of 2-(3-benzyloxybenzamido)benzenesulfonamide produced in Reference Example 1, and the mixture was stirred for 1 hour. This solution was mixed with 121 mg (1.54 mmol) of acetyl chloride and stirred at room temperature for 3 hours. After completion of the reaction, this was neutralized by adding an ammonium chloride aqueous solution and then the solvent was evaporated. The resulting residue was extracted with ethyl acetate, washed with water and saturated brine and dried over anhydrous sodium sulfate, and then the solvent was evaporated under a reduced pressure. The resulting residue was purified by a silica gel column chromatography to obtain 160 mg (yield: 35%) of the title compound.

NMR (DMSO-d$_6$) δ: 1.99 (3H, s), 5.20 (2H, s), 7.28–7.62 (10H, m), 7.76 (1H, dd, J=8 Hz, 8 Hz), 7.95 (1H, dd, J=8 Hz, 1 Hz), 8.41 (1H, dd, J=8 Hz, 1 Hz), 10.45 (1H, s), 12.58 (1H, s)

IR (ν, cm$^{-1}$, KBr): 3342, 3118, 2871, 1708, 1660, 1585, 1531, 1444, 1162, 1029, 862, 752, 694

EI-MS (m/z, %): 424 (M$^+$, 69), 365 (13), 303 (27), 302 (22), 301 (10), 212 (16), 211 (71), 210 (20), 183 (16)

Melting point: 195–196° C.

Example 4

N-[2-(3-Benzyloxybenzamido)benzenesulfonyl]-4-trifluoromethylbenzamide

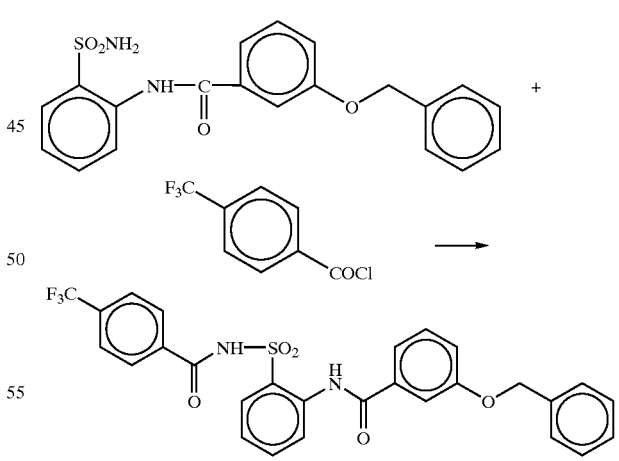

A 275 mg (0.72 mmol) portion of 2-(3-benzyloxybenzamido)benzenesulfonamide produced in Reference Example 1, 0.24 ml (1.44 mmol) of 4-trifluoromethylbenzyl chloride and 300 mg (2.16 mmol) of potassium carbonate were dissolved in water-dioxane 1:1 (10 ml), and the solution was stirred for 18 hours. The solvent was evaporated, the resulting residue was extracted with ethyl acetate, washed with water and saturated brine and dried over anhydrous sodium sulfate, and then the solvent was evaporated under a reduced pressure. The resulting residue was purified by a silica gel column chromatography to obtain 322 mg (yield: 88%) of the title compound.

NMR (CDCl$_3$) δ: 5.13 (2H, s), 7.18 (1H, dd, J=6 Hz, 1 Hz), 7.23–7.43 (7H, m), 7.64–7.72 (5H, m), 7.85 (2H, d, J=8 Hz), 8.02 (1H, dd, J=6 Hz, 1 Hz), 8.75 (1H, dd, J=6 Hz, 1 Hz), 9.25 (1H, br-s), 10.53 (1H, br-s)

IR (ν, cm$^{-1}$, KBr): 1698, 1658, 1536, 1478, 1442, 1358, 1324, 1310, 1174

EI-MS (m/z, %): 554 (M$^+$, 14), 368 (7), 211 (15), 173 (13)

Melting point: 220–221° C.

Example 5

N-[2-(3-Benzyloxybenzamido)benzenesulfonyl]-4-nitrobenzamide

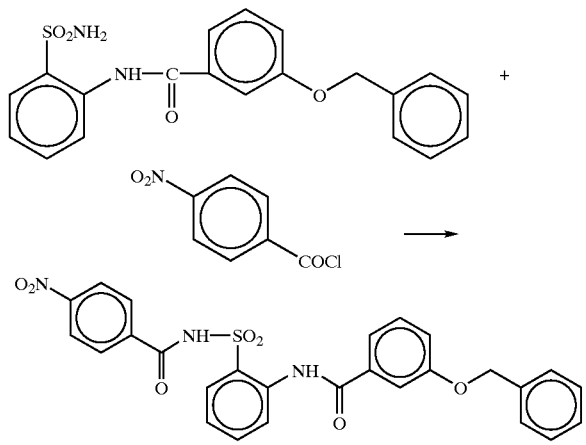

A 300 mg (0.78 mmol) portion of 2-(3-benzyloxybenzamido)benzenesulfonamide produced in Reference Example 1, 290 mg (1.56 mmol) of 4-nitrobenzoyl chloride and 325 mg (2.34 mmol) of potassium carbonate were dissolved in water-dioxane 1:1 mixture (10 ml), and the solution was stirred for 18 hours. The solvent was evaporated, the resulting residue was extracted with ethyl acetate, washed with water and saturated brine and dried over anhydrous sodium sulfate, and then the solvent was evaporated under a reduced pressure. The resulting residue was purified by a silica gel column chromatography to obtain 320 mg (yield: 77%) of the title compound.

NMR (CDCl$_3$) δ: 5.14 (2H, s), 7.20 (1H, dd, J=6 Hz, 1 Hz), 7.22–7.46 (7H, m), 7.64 (1H, d, J=6 Hz), 7.65–7.70 (2H, m), 7.90 (2H, d, J=8 Hz), 8.04 (1H, d, J=6 Hz), 8.25 (2H, d, J=8 Hz), 8.74 (1H, d, J=6 Hz), 9.25 (1H, br-s), 10.53 (1H, br-s)

IR (ν, cm$^{-1}$, KBr): 1696, 1662, 1608, 1474, 1442, 1344, 1320, 1276, 1250

EI-MS (m/z, %): 531 (M$^+$, 3), 303 (3), 212 (4), 211 (12)

Melting point: 233–234° C.

Example 6

N-[2-(3-Benzyloxybenzamido)benzenesulfonyl]-4-methoxybenzamide

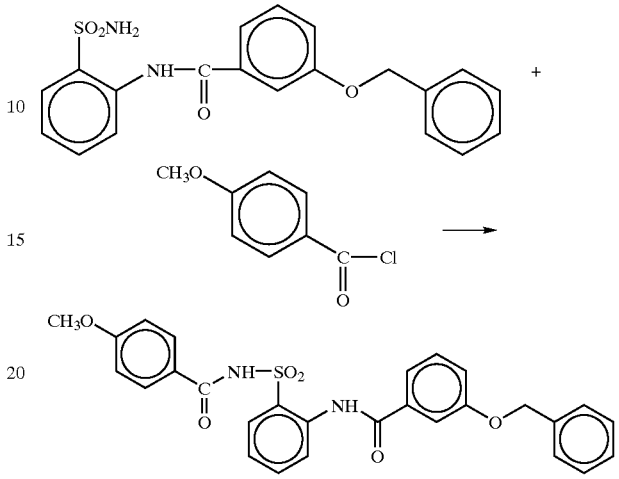

A 300 mg (0.78 mmol) portion of 2-(3-benzyloxybenzamido)benzenesulfonamide produced in Reference Example 1, 267 mg (1.56 mmol) of 4-methoxybenzoyl chloride and 325 mg (2.34 mmol) of potassium carbonate were dissolved in water-dioxane 1:1 mixture (10 ml), and the solution was stirred for 18 hours. The solvent was evaporated, the resulting residue was extracted with ethyl acetate, washed with water and saturated brine and dried over anhydrous sodium sulfate, and then the solvent was evaporated under a reduced pressure. The resulting residue was purified by a silica gel column chromatography to obtain 282 mg (yield: 70%) of the title compound.

NMR (CDCl$_3$) δ: 3.38 (3H, s), 5.14 (2H, s), 6.90 (2H, d, J=8 Hz), 7.19 (1H, dd, J=7 Hz, 1 Hz), 7.22–7.46 (8H, m), 7.64–7.74 (3H, m), 7.77 (1H, m), 8.02 (1H, dd, J=7 Hz, 1 Hz), 8.73 (1H, br-s), 8.76 (1H, dd, J=7 Hz, 1 Hz), 10.63 (1H, br-s)

IR (ν, cm$^{-1}$, KBr): 1702, 1688, 1606, 1582, 1536, 1516, 1490, 1472, 1444, 1414, 1344, 1310, 1270, 1248

EI-MS (m/z, %): 516 (M$^+$, 4), 424 (4), 303 (6), 302 (4), 212 (5), 211 (14)

Melting point: 189–190° C.

Example 7

N-[2-(3-Benzyloxybenzamido)benzenesulfonyl] cyclohexamide

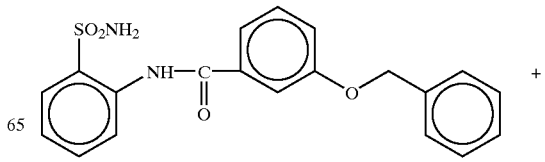

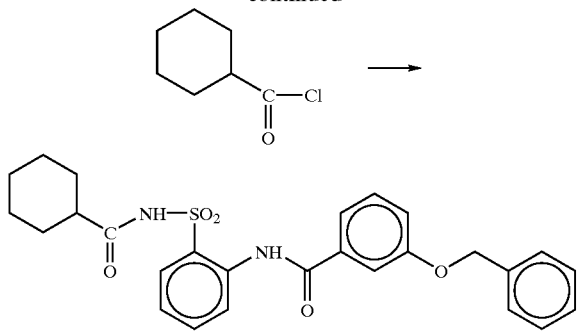

In a stream of nitrogen and under ice-cooling, 196 mg (1.56 mmol) of potassium tert-butoxide was added to an anhydrous tetrahydrofuran (10 ml) solution containing 300 mg (0.78 mmol) of 2-(3-benzyloxybenzamido)benzenesulfonamide produced in Reference Example 1, and the mixture was stirred for 1 hour. This solution was mixed with 176 mg (1.19 mmol) of cyclohexanecarbonyl chloride and stirred at room temperature for 3 hours. After completion of the reaction, this was neutralized by adding an ammonium chloride aqueous solution and then the solvent was evaporated. The resulting residue was extracted with ethyl acetate, washed with water and saturated brine and dried over anhydrous sodium sulfate, and then the solvent was evaporated under a reduced pressure. The resulting residue was purified by a silica gel column chromatography to obtain 257 mg (yield: 67%) of the title compound.

NMR (CDCl$_3$) δ: 1.03–1.39 (4H, m), 1.53–1.80 (6H, m), 2.04–2.18 (1H, m), 3.13 (2H, s), 7.17 (1H, dd, J=6 Hz, 1 Hz), 7.21–7.25 (1H, m), 7.31–7.43 (6H, m), 7.61–7.69 (2H, m), 7.70–7.72 (1H, m), 7.96 (1H, dd, J=6 Hz, 1 Hz), 8.49 (1H, s), 8.70 (1H, d, J=6 Hz), 10.46 (1H, s)

IR (ν, cm$^{-1}$, KBr): 1710, 1662, 1582, 1530, 1488, 1476, 1448, 1382, 1342, 1304, 1274, 1246

EI-MS (m/z, %): 492 (M$^+$, 82), 382 (39), 302 (45), 211 (84), 91 (100)

Example 8

N-[2-(3-Benzyloxybenzamido)benzenesulfonyl]-n-hexanamide

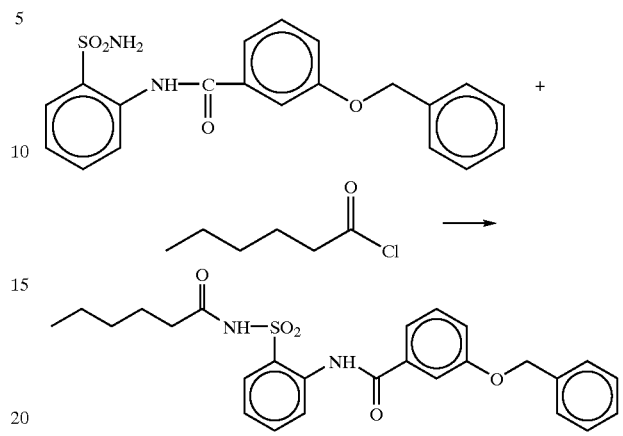

In a stream of nitrogen and under ice-cooling, 210 mg (1.67 mmol) of potassium tert-butoxide was added to an anhydrous tetrahydrofuran (10 ml) solution containing 300 mg (0.78 mmol) of 2-(3-benzyloxybenzamido)benzenesulfonamide produced in Reference Example 1, and the mixture was stirred for 1 hour. This solution was mixed with 176 mg (1.19 mmol) of n-hexanoyl chloride and stirred at room temperature for 3 hours. After completion of the reaction, this was neutralized by adding an ammonium chloride aqueous solution and then the solvent was evaporated. The resulting residue was extracted with ethyl acetate, washed with water and saturated brine and dried over anhydrous sodium sulfate, and then the solvent was evaporated under a reduced pressure. The resulting residue was purified by a silica gel column chromatography to obtain 300 mg (yield: 86%) of the title compound.

NMR (CDCl$_3$) δ: 0.80 (3H, t, J=7 Hz), 1.13–1.23 (4H, m), 1.47–1.58 (2H, m), 2.20 (2H, t, J=7 Hz), 5.13 (2H, s), 7.16 (1H, d, J=6 Hz, 1 Hz), 7.21–7.25 (1H, m), 7.30–7.72 (6H, m), 7.61–7.72 (3H, m), 7.96 (1H, dd, J=6 Hz, 1 Hz), 8.47 (1H, br-s), 8.70 (1H, dd, J=6 Hz, 1 Hz), 10.45 (1H, s)

IR (ν, cm$^{-1}$, KBr): 1710, 1660, 1606, 1588, 1538, 1472, 1430, 1316, 1272

EI-MS (m/z, %): 480 (M$^+$, 57), 382 (27), 302 (31), 211 (71), 91 (100)

Melting point: 133–134° C.

Example 9

N-[2-(3-Benzyloxybenzamido)benzenesulfonyl]decanamide

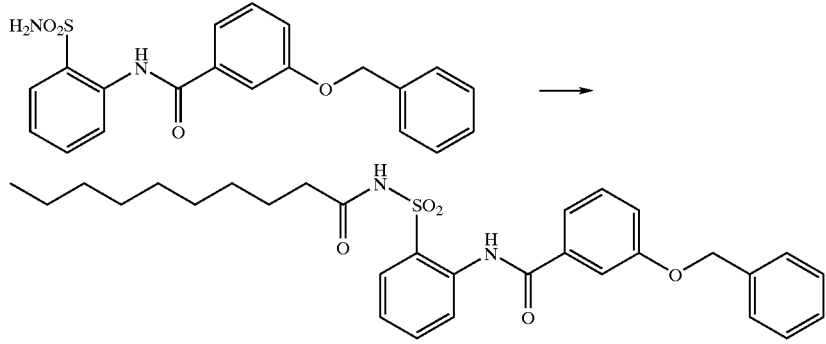

In a stream of nitrogen and at 0° C., 117 mg (1.04 mmol) of potassium t-butoxide was added to an anhydrous tetrahydrofuran (10 ml) solution containing 200 mg (0.52 mmol) of 3-benzyloxy-N-(2-sulfamoylphenyl)benzamide produced in Reference Example 1, and the mixture was stirred for 1 hour. Next, this solution was mixed with 0.16 ml (0.78 mmol) of decanoyl chloride and stirred at room temperature for 3 hours. After completion of the reaction, this was neutralized by adding an ammonium chloride aqueous solution and then the solvent was evaporated. The resulting residue was extracted with ethyl acetate, washed with water and saturated brine in that order and dried over anhydrous sodium sulfate, and then the solvent was evaporated under a reduced pressure. The resulting residue was purified by a silica gel column chromatography to obtain 150 mg (yield: 50.0%) of the title compound.

NMR (CDCl$_3$) δ: 0.80 (3H, t, J=7 Hz), 1.17–1.26 (12H, m), 1.50–1.59 (2H, m), 2.21 (2H, t, J=7 Hz), 5.14 (2H, s), 7.17 (1H, dd, J=8 Hz, 1 Hz), 7.24 (1H, ddd, J=8 Hz, 8 Hz, 1 Hz), 7.31–7.48 (8H, m), 7.61–7.72 (3H, m), 7.98 (1H, dd, J=8 Hz, 2 Hz), 8.30 (1H, br-s), 8.72 (1H, d, J=8 Hz), 10.43 (1H, s)

IR (ν, cm$^{-1}$, KBr): 1704, 1662, 1606, 1588, 1540, 1472, 1342, 1166 FAB-MS (neg: m/z, %): 535 ([M–H]+100)

Melting point: 85–86° C.

Example 10

N-[2-(3-Benzyloxybenzamido)benzenesulfonyl] pentafluorobenzamide

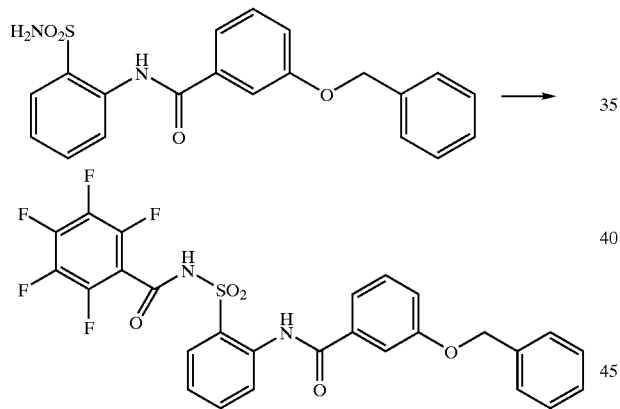

A 300 mg (0.78 mmol) portion of 3-benzyloxy-N-(2-sulfamoylphenyl)benzamide produced in Reference Example 1, 271 mg (1.18 mmol) of pentafluorobenzoyl chloride and 374 mg (2.70 mmol) of potassium carbonate were dissolved in mixed solvent (10 ml) of water and dioxane (1:1) and stirred at room temperature for 18 hours. After completion of the reaction, the solvent was evaporated under a reduced pressure. The resulting residue was extracted with ethyl acetate, washed with water and saturated brine in that order and dried over anhydrous sodium sulfate, and then the solvent was evaporated under a reduced pressure. The resulting residue was purified by a silica gel column chromatography to obtain 350 mg (yield: 77.0%) of the title compound.

NMR (CDCl$_3$) δ: 5.14 (2H, s), 7.19 (1H, ddd, J=8 Hz, 2 Hz, 1 Hz), 7.31–7.48 (7H, m), 7.60 (1H, ddd, J=8 Hz, 2 Hz, 1 Hz), 7.66 (1H, dd, J=2 Hz, 1 Hz), 7.73 (1H, ddd, J=8 Hz, 8 Hz, 1 Hz), 8.06 (1H, dd, J=8 Hz, 1 Hz), 8.76 (1H, dd, J=1 Hz), 10.31 (1H, s)

EI-MS (m/z, %): 576 (m+, 20), 211 (14), 91 (100)

IR (ν, cm$^{-1}$, KBr): 1704, 1654, 1582, 1536, 1506, 1440

Example 11

N-[2-(3-Benzyloxybenzamido)benzenesulfonyl]-2,4-difluorobenzamide

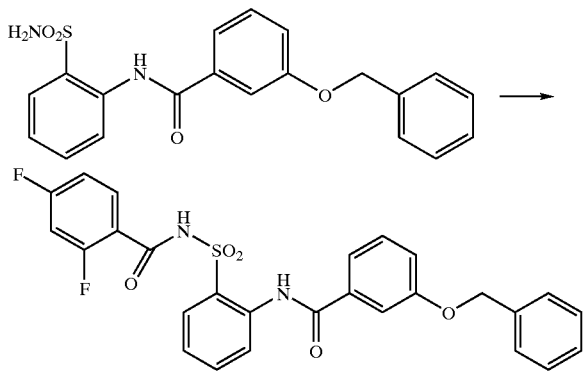

A 300 mg (0.78 mmol) portion of benzyloxy-N-(2-sulfamoylphenyl)benzamide, 273 mg (1.55 mmol) of 2,4-difluorobenzoyl chloride and 374 mg (2.70 mmol) of potassium carbonate were dissolved in a mixed solvent (10 ml) of water and dioxane (1:1) and stirred at room temperature for 18 hours. After completion of the reaction, the solvent was evaporated under a reduced pressure. The resulting residue was extracted with ethyl acetate, washed with water and saturated brine in that order and dried over anhydrous sodium sulfate, and then the solvent was evaporated under a reduced pressure. The resulting residue was purified by a silica gel column chromatography to obtain 350 mg (yield: 86.0%) of the title compound.

NMR (CDCl$_3$) δ: 5.15 (2H, s), 6.92 (1H, ddd, J=8 Hz, 8 Hz, 2 Hz), 7.05 (1H, ddd, J=8 Hz, 8 Hz, 2 Hz), 7.17 (1H, ddd, J=8 Hz, 8 Hz, 1 Hz), 7.22 (1H, ddd, J=8 Hz, 2 Hz, 1 Hz), 7.30–7.50 (7H, m), 7.58 (1H, dd, J=8 Hz, 1 Hz), 7.70 (1H, dd, J=2 Hz, 1 Hz), 7.73–7.78 (1H, m), 7.83 (1H, dd, J=8 Hz, 2 Hz), 8.41 (1H, dd, J=8 Hz, 1 Hz), 11.36 (1H, s)

IR (ν, cm$^{-1}$, KBr): 1678, 1608, 1580, 1546, 1498 FAB-MS (neg: m/z, %): 521 ([M–H]+100)

Melting point: 208–209° C.

Reference Example 2

3-(4-t-Butylbenzyloxy)-N-(2-sulfamoylphenyl) benzamide

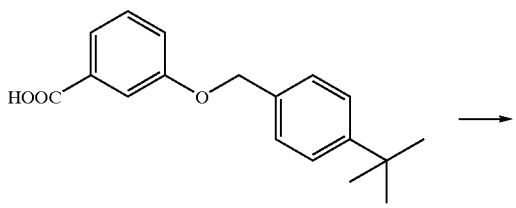

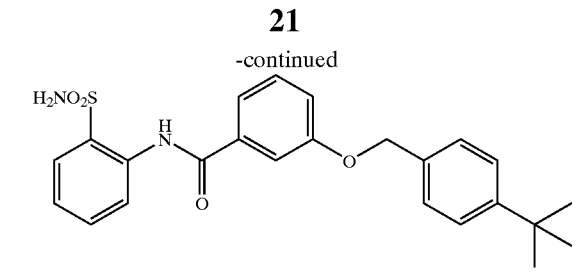

A benzene (30 ml) solution containing 4.00 g (14.0 mmol) of 3-(4-t-butylbenzyloxy)benzoic acid and 3 ml of thionyl chloride was heated under reflux for 2 hours and then the solvent was evaporated under a reduced pressure. The resulting residue was dissolved in methylene chloride (30 ml), this solution was added dropwise under ice-cooling to a pyridine (50 ml) solution containing 2.42 g (14.0 mmol) of 2-aminobenzenesulfonamide, the mixture was stirred at room temperature for 18 hours and then methylene chloride was evaporated under a reduced pressure. The resulting residue was dissolved in ethyl acetate, washed with a 1 N hydrochloric acid aqueous solution, water and saturated brine in that order and dried over anhydrous sodium sulfate, and then the solvent was evaporated under a reduced pressure. The thus obtained crude crystals were recrystallized from an ether-hexane mixed solvent to obtain 4.2 g (yield: 68.0%) of the title compound.

NMR (CDCl$_3$) δ: 1.38 (9H, s), 4.92 (2H, s), 5.09 (2H, s), 7.16 (1H, ddd, J=8 Hz, 2 Hz, 1 Hz), 7.23 (1H, ddd, J=8 Hz, 8 Hz, 2 Hz), 7.36–7.44 (5H, m), 7.49 (1H, dd, J=8 Hz, 1 Hz), 7.56–7.63 (2H, m), 7.94 (1H, dd, J=8 Hz, 2 Hz), 8.53 (1H, dd, J=8 Hz, 1 Hz), 10.04 (1H, s)

EI-MS (m/z, %): 438 (m+, 37), 147 (100), 132 (84), 117 (65)

IR (ν, cm$^{-1}$, KBr): 1674, 1658, 1586, 1538, 1446, 1332, 1168

Melting point: 117–118° C.

Example 12

N-[2-[3-(4-t-Butylbenzyloxy)benzamido]benzenesulfonyl]pivalamide

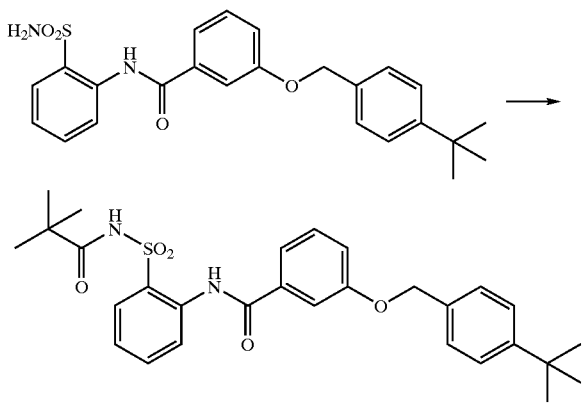

In a stream of nitrogen and at 0° C., 0.09 ml (0.75 mmol) of pivaloyl chloride was added to an anhydrous tetrahydrofuran (10 ml) solution containing 300 mg (0.68 mmol) of 3-(4-t-butylbenzyloxy)-N-(2-sulfamoylphenyl)benzamide produced in Reference Example 2 and 167 mg (1.36 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 284 mg (yield: 80.0%) of the title compound.

NMR (CDCl$_3$) δ: 1.14 (9H, s), 1.33 (9H, s), 5.10 (2H, s), 7.18 (1H, dd, J=8 Hz, 2 Hz), 7.25 (1H, ddd, J=8 Hz, 8 Hz, 2 Hz), 7.38–7.45 (10H, m), 7.63 (1H, dd, J=8 Hz, 2 Hz), 7.67 (1H, ddd, J=8 Hz, 8 Hz, 2 Hz), 7.72–7.75 (1H, m), 7.97 (1H, dd, J=8 Hz, 2 Hz), 8.27 (1H, br-s), 8.72 (1H, dd, J=8 Hz, 2 Hz), 10.41 (1H, s)

IR (ν, cm$^{-1}$, KBr): 1702, 1660, 1580, 1538, 1478, 1448, 1342, 1312, 1292

EI-MS (m/z, %): 522 (m+, 72), 147 (100)

Melting point: 193–194° C.

Example 13

N-[2-[3-(4-t-Butylbenzyloxy)benzamido]benzenesulfonyl]cinnamamide

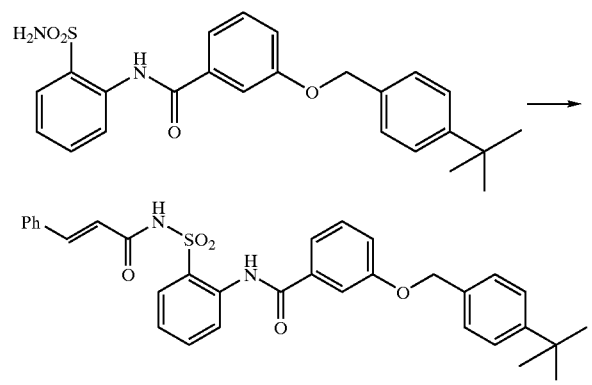

In a stream of nitrogen and at 0° C., 126 mg (0.75 mmol) of cinnamoyl chloride was added to an anhydrous tetrahydrofuran (10 ml) solution containing 300 mg (0.68 mmol) of 3-(4-t-butylbenzyloxy)-N-(2-sulfamoylphenyl)benzamide produced in Reference Example 2 and 167 mg (1.36 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting crude crystals were washed with methanol to obtain 370 mg (yield: 95.0%) of the title compound.

NMR (CDCl$_3$) δ: 1.31 (9H, s), 5.11 (2H, s), 6.31 (1H, d, J=16 Hz), 7.17 (1H, ddd, J=8 Hz, 2 Hz, 1 Hz), 7.24 (1H, ddd, J=8 Hz, 8 Hz, 1 Hz), 7.31–7.44 (10H, m), 7.64–7.70 (3H, m), 7.77–7.78 (1H, m), 8.01 (1H, dd, J=8 Hz, 2 Hz), 8.74 (1H, dd, J=8 Hz, 1 Hz), 10.60 (1H, s)

IR (ν, cm⁻¹, KBr): 1688, 1668, 1630, 1582, 1534, 1476, 1442, 1334, 1310, 1272

EI-MS (m/z, %): 568 (m+, 3), 437 (3), 147 (100)

Melting point: 110–111° C.

Example 14

N-[2-(3-Benzyloxybenzamido)benzenesulfonyl] oleinamide

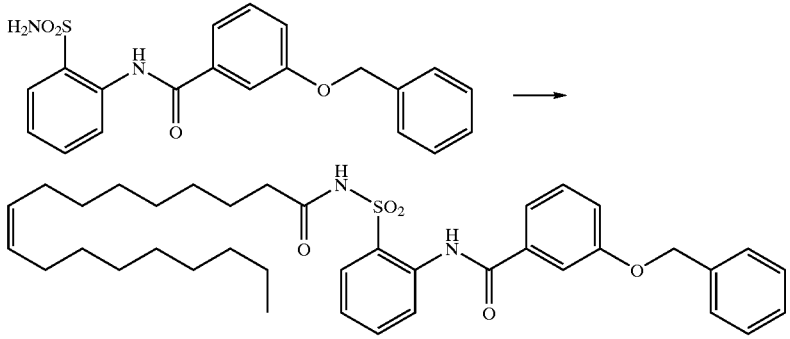

In a stream of nitrogen and at 0° C., 787 mg (2.62 mmol) of oleyl chloride was added to an anhydrous tetrahydrofuran (10 ml) solution containing 500 mg (1.30 mmol) of 3-benzyloxy-(2-sulfamoylphenyl)benzamide produced in Reference Example 1 and 480 mg (3.93 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 625 mg (yield: 74.0%) of the title compound.

NMR (CDCl₃) δ: 0.87 (3H, t, J=7 Hz), 1.15–1.38 (19H, m), 1.45–1.62 (4H, m), 1.85–2.01 (3H, m), 2.20 (2H, t, J=7 Hz), 5.14 (2H, s), 5.30–5.42 (2H, m), 7.17 (1H, ddd, J=8 Hz, 2 Hz, 1 Hz), 7.50 (1H, ddd, J=8 Hz, 8 Hz, 1 Hz), 7.31–7.48 (6H, m), 7.61–7.72 (3H, m), 7.78 (1H, dd, J=8 Hz, 2 Hz), 8.31 (1H, br-s), 8.72 (1H, dd, J=8 Hz, 1 Hz), 10.43 (1H, s)

IR (ν, cm⁻¹, KBr): 1708, 1660, 1606, 1588, 1542, 1472, 1448, 1338

EI-MS (m/z, %): 646 (m+, 14), 383 (57), 302 (12), 211 (97), 91 (100)

Melting point: 82–83° C.

Example 15

N-[2-(3-Benzyloxybenzamido)benzenesulfonyl] linolamide

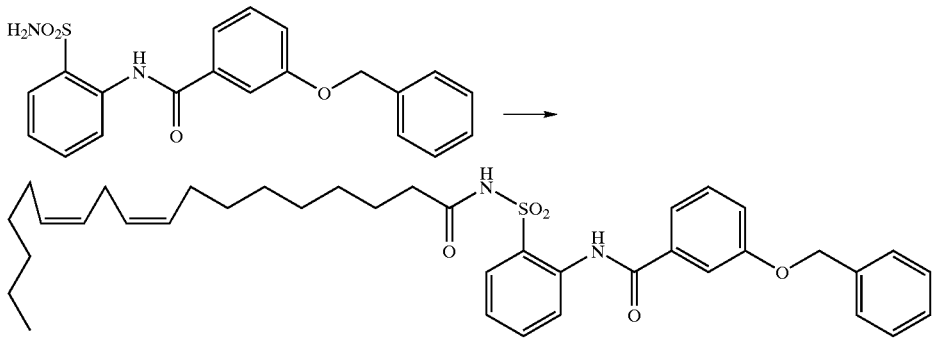

A benzene (30 ml) solution containing 440 mg (1.57 mmol) of linoleic acid and 3 ml of thionyl chloride was heated under reflux for 2 hours, and then the solvent was evaporated under a reduced pressure. The thus obtained residue was dissolved in anhydrous tetrahydrofuran (10 ml), this solution was added dropwise under ice-cooling to an anhydrous tetrahydrofuran (10 ml) solution containing 500 mg (1.30 mmol) of 3-benzyloxy-N-(2-sulfamoylphenyl) benzamide produced in Reference Example 1 and 352 mg (2.88 mmol) of 4-dimethylaminopyridine, and the mixture was stirred at room temperature for 1 hour. After evaporation of the solvent under a reduced pressure, the resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 625 mg (yield: 74.0%) of the title compound.

NMR (CDCl₃) δ: 0.88 (3H, t, J=7 Hz), 1.10–1.38 (12H, m), 1.40–1.70 (4H, m), 1.93–2.10 (4H, m), 2.20 (2H, t, J=8

Hz), 2.74 (2H, dd, J=6 Hz, 6 Hz), 5.13 (2H, s), 5.25–5.42 (4H, m), 7.16 (1H, dd, J=8 Hz, 2 Hz), 7.24 (1H, ddd, J=8 Hz, 8 Hz, 1 Hz), 7.30–7.50 (6H, m), 7.60–7.71 (3H, m), 7.96 (1H, dd, J=8 Hz, 2 Hz), 8.43 (1H, br-s), 8.70 (1H, dd, J=8 Hz, 1 Hz), 10.45 (1H, s)

IR (ν, cm⁻¹, KBr): 1714, 1660, 1606, 1588, 1540, 1472, 1448, 1338 FAB-MS (neg: m/z, %): 643 ([M−H]+100)

Reference Example 3

3-Benzyloxy-4-nitro-N-(2-sulfamoylphenyl)benzamide

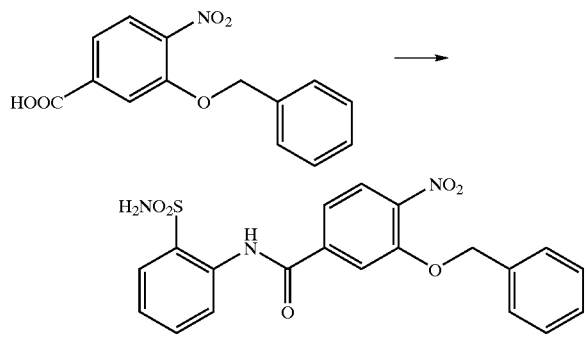

A benzene (30 ml) solution containing 2.00 g (7.30 mmol) of 3-benzyloxy-4-nitrobenzoic acid and 3 ml of thionyl chloride was heated under reflux for 2 hours and then the solvent was evaporated under a reduced pressure. The resulting residue was dissolved in methylene chloride (30 ml), this solution was added dropwise under ice-cooling to a pyridine (50 ml) solution containing 1.38 g (8.00 mmol) of 2-aminobenzenesulfonamide, the mixture was stirred at room temperature for 18 hours and then methylene chloride was evaporated under a reduced pressure. The resulting residue was dissolved in ethyl acetate, washed with a 1 N hydrochloric acid aqueous solution, water and saturated brine in that order and dried over anhydrous sodium sulfate, and then the solvent was evaporated under a reduced pressure. The thus obtained crude crystals were washed with methanol to obtain 2.50 g (yield: 80.0%) of the title compound.

NMR (DMSO-d₆) δ: 5.41 (2H, s), 7.34–7.52 (6H, m), 7.61 (1H, dd, J=8 Hz, 2 Hz), 7.69 (1H, ddd, J=8 Hz, 8 Hz, 2 Hz), 7.91–7.96 (2H, m), 8.11 (1H, d, J=8 Hz), 8.33 (1H, d, J=8 Hz), 10.41 (1H, s)

Example 16

N-[2-(3-Benzyloxy-4-nitrobenzamido)benzenesulfonyl]decanamide

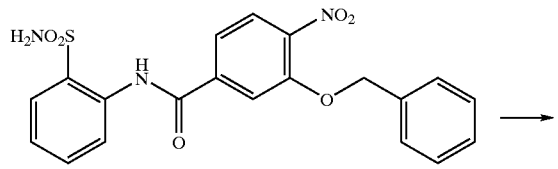

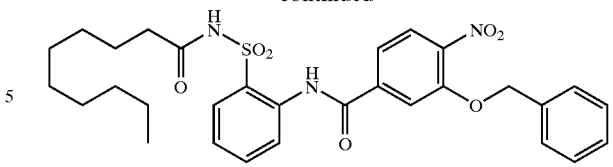

In a stream of nitrogen and at 0° C., 0.24 ml (1.16 mmol) of decanoyl chloride was added to an anhydrous tetrahydrofuran (10 ml) solution containing 435 mg (1.02 mmol) of 3-benzyloxy-4-nitro-N-(2-sulfamoylphenyl)benzamide produced in Reference Example 3 and 274 mg (2.23 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 490 mg (yield: 83.0%) of the title compound.

NMR (CDCl₃) δ: 0.86 (3H, t, J=7 Hz), 1.10–1.30 (12H, m), 1.48–1.65 (2H, m), 2.25 (2H, t, J=7 Hz), 5.32 (2H, s), 7.24–7.43 (4H, m), 7.47–7.51 (2H, m), 7.68–7.74 (2H, m), 7.92–7.99 (3H, m), 8.71 (1H, dd, J=8 Hz, 2 Hz), 10.64 (1H, s)

IR (ν, cm⁻¹, KBr): 1722, 1668, 1614, 1588, 1538, 1472, 1444, 1404, 1342, 1322, 1292

EI-MS (m/z, %): 581 (m+, 2), 321 (11), 211 (2), 91 (100)

Melting point: 129–130° C.

Reference Example 4

3-(4-Chlorobenzyloxy)-N-(2-sulfamoylphenyl)benzamide

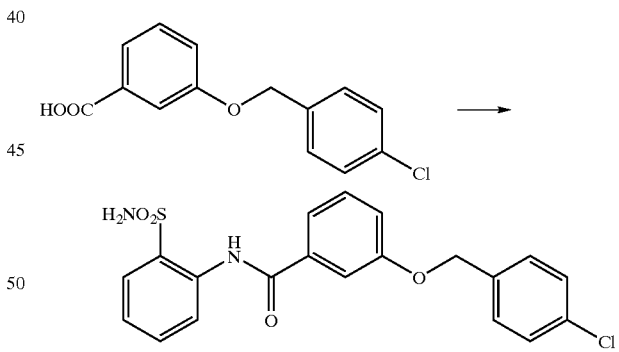

A benzene (30 ml) solution containing 4.00 g (15.2 mmol) of 3-(4-chlorobenzyloxy)benzoic acid and 3 ml of thionyl chloride was heated under reflux for 2 hours and then the solvent was evaporated under a reduced pressure. The resulting residue was dissolved in methylene chloride (30 ml), this solution was added dropwise under ice-cooling to a pyridine (50 ml) solution containing 2.75 g (16.0 mmol) of 2-aminobenzenesulfonamide, the mixture was stirred at room temperature for 18 hours and then methylene chloride was evaporated under a reduced pressure. The resulting residue was dissolved in ethyl acetate, washed with a 1 N hydrochloric acid aqueous solution, water and saturated brine in that order and dried over anhydrous sodium sulfate, and then the solvent was evaporated under a reduced pressure. The thus obtained crude crystals were washed with methanol to obtain 4.70 g (yield: 74.0%) of the title compound.

NMR (DMSO-d$_6$) δ: 5.20 (2H, s), 7.27–7.31 (1H, m), 7.34 (1H, ddd, J=8 Hz, 8 Hz, 2 Hz), 7.45–7.56 (7H, m), 7.65 (1H, ddd, J=8 Hz, 8 Hz, 2 Hz), 7.77 (2H, s), 7.92 (1H, dd, J=8 Hz, 2 Hz), 8.47 (1H, dd, J=8 Hz, 1 Hz), 10.38 (1H, s)

EI-MS (m/z, %): 418 (m+2, 6), 416 (m+, 17)

IR (ν, cm$^{-1}$, KBr): 1672, 1586, 1542, 1446, 1154

Melting point: 174–175° C.

Example 17

N-[2-[3-(4-Chlorobenzyloxy)benzamido]benzenesulfonyl]acetamide

In a stream of nitrogen and at 0° C., 0.12 ml (1.30 mmol) of acetic anhydride was added to an anhydrous tetrahydrofuran (10 ml) solution containing 500 mg (1.20 mmol) of 3-(4-chlorobenzyloxy)-N-(2-sulfamoylphenyl)benzamide produced in Reference Example 4 and 293 mg (2.40 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was recrystallized from an ethyl acetate-diethyl ether mixed solvent to obtain 290 mg (yield: 52.7%) of the title compound.

NMR (CDCl$_3$) δ: 2.06 (3H, s), 5.11 (2H, s), 7.16 (1H, ddd, J=8 Hz, 2 Hz, 1 Hz), 7.23–7.29 (1H, m), 7.34–7.44 (5H, m), 7.61–7.72 (3H, m), 7.98 (1H, dd, J=8 Hz, 1 Hz), 8.18 (1H, br-s), 8.73 (1H, dd, J=8 Hz, 1 Hz), 10.41 (1H, br-s)

IR (ν, cm$^{-1}$, KBr): 3768, 3108, 2872, 1716, 1666, 1580, 1538, 1478, 1448

EI-MS (m/z, %): 460 (9), 458 (23), 336 (5), 245 (11), 183 (6), 127 (53), 125 (100), 92 (10)

Melting point: 176–179° C.

Example 18

N-[2-[3-(4-Chlorobenzyloxy)benzamido]benzenesulfonyl]hexanamide

In a stream of nitrogen and at 0° C., 0.18 ml (1.30 mmol) of hexanoyl chloride was added to an anhydrous tetrahydrofuran (10 ml) solution containing 500 mg (1.2 mmol) of 3-(4-chlorobenzyloxy)-N-(2-sulfamoylphenyl)benzamide produced in Reference Example 4 and 293 mg (2.40 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 600 mg (yield: 97%) of the title compound.

NMR (CDCl$_3$) δ: 0.81 (3H, t, J=7 Hz), 1.13–1.28 (4H, m), 1.48–1.60 (2H, m), 2.22 (2H, t, J=7 Hz), 5.11 (2H, s), 7.15 (1H, ddd, J=8 Hz, 2 Hz, 1 Hz), 7.23–7.28 (1H, m), 7.34–7.43 (5H, m), 7.62–7.70 (1H, m), 7.97 (1H, dd, J=8 Hz, 2 Hz), 8.21 (1H, br-s), 8.73 (1H, dd, J=8 Hz, 1 Hz), 10.45 (1H, br-s)

IR (ν, cm$^{-1}$, KBr): 3392, 3080, 2952, 2932, 2868, 1720, 1658, 1580, 1536, 1486, 1474, 1448, 1412

EI-MS (m/z, %): 526 (4), 514 (8), 336 (4), 245 (9), 183 (4), 127 (31), 125 (100)

Melting point: 148–149° C.

Example 19

N-[2-[3-(4-Chlorobenzyloxy)benzamido]benzenesulfonyl]decanamide

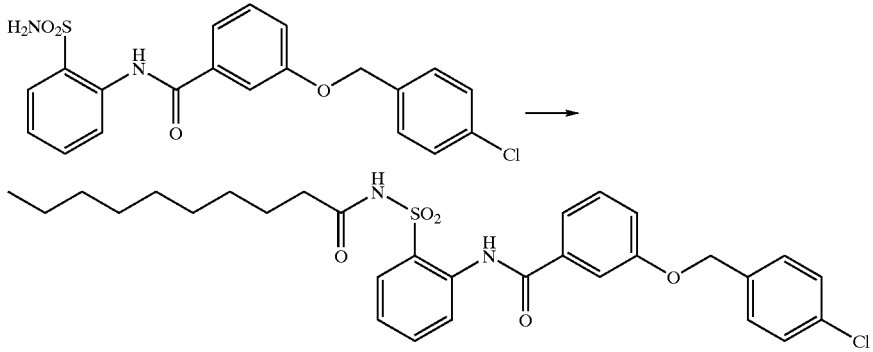

In a stream of nitrogen and at 0° C., 0.27 ml (1.30 mmol) of decanoyl chloride was added to an anhydrous tetrahydrofuran (10 ml) solution containing 500 mg (1.20 mmol) of 3-(4-chlorobenzyloxy)-N-(2-sulfamoylphenyl)benzamide produced in Reference Example 4 and 293 mg (2.40 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 640 mg (yield: 93.0%) of the title compound.

NMR (CDCl$_3$) δ: 0.86 (3H, t, J=7 Hz), 1.15–1.30 (12H, m), 1.48–1.59 (2H, m), 2.22 (2H, t, J=7 Hz), 5.11 (2H, s), 7.15 (1H, ddd, J=8 Hz, 2 Hz, 1 Hz), 7.23–7.28 (1H, m), 7.34–7.44 (5H, m), 7.62–7.70 (3H, m), 7.97 (1H, dd, J=8 Hz, 1 Hz), 8.18 (1H, br-s), 8.73 (1H, dd, J=8 Hz, 1 Hz), 10.45 (1H, br-s)

IR (ν, cm$^{-1}$, KBr): 3368, 3032, 2920, 2852, 1702, 1662, 1604, 1586, 1542, 1494, 1472, 1448, 1438

EI-MS (m/z, %); 572 (2), 570 (4), 336 (4), 245 (10), 183 (3), 127 (32), 125 (100)

Melting point: 159–161° C.

Reference Example 5

3-(4-Nitrobenzyloxy)-N-(2-sulfamoylphenyl)benzamide

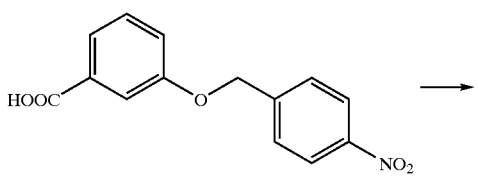

-continued

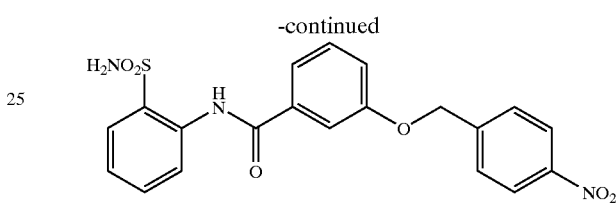

A benzene (20 ml) solution containing 1.40 (5.1 mmol) of 3-(4-nitrobenzyloxy)benzoic acid and 2 ml of thionyl chloride was heated under reflux for 2 hours and then the solvent was evaporated under a reduced pressure. The resulting residue was dissolved in methylene chloride (20 ml), this solution was added dropwise under ice-cooling to a pyridine (30 ml) solution containing 0.97 g (5.6 mmol) of 2-aminobenzenesulfonamide, the mixture was stirred at room temperature for 18 hours and then methylene chloride was evaporated under a reduced pressure. The resulting residue was dissolved in ethyl acetate, washed with a 1 N hydrochloric acid aqueous solution, water and saturated brine in that order and dried over anhydrous sodium sulfate, and then the solvent was evaporated under a reduced pressure. The thus obtained crude crystals were washed with methanol to obtain 1.9 g (yield: 87.0%) of the title compound.

NMR (DMSO-d$_6$) δ: 5.39 (2 H, s), 7.30–7.38 (2 H, m), 7.50–7.58 (3 H, m), 7.65 (1 H, ddd, J=8 Hz, 8 Hz, 2 Hz), 7.75–7.80 (4 H, m), 7.91 (1 H, dd, J=8 Hz, 2 Hz), 8.25–8.30 (2 H, m), 8.46 (1 H, dd, J=8, 1 Hz), 10.38 (1 H, s)

EI-MS (m/z, %): 427 (m+, 23 ), 347 (82), 256 (100), 121 (50)

IR (ν, cm$^{-1}$, KBr): 1658, 1590, 1530, 1446, 1344, 1152, 1046

Melting point: 177–178° C.

Example 20

**N-[2-[3-(4-Nitrobenzyloxy)benzamido]
benzenesulfonyl]acetamide**

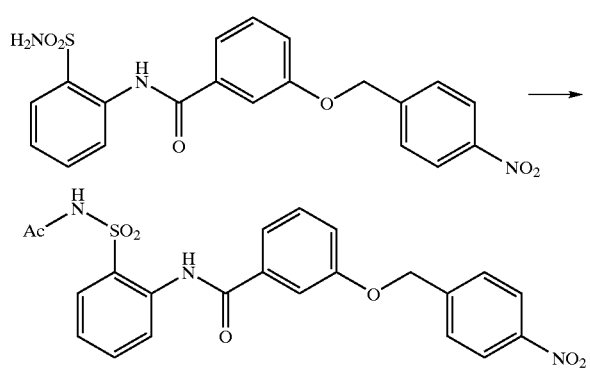

In a stream of nitrogen and at 0° C. 0.07 ml (0.80 mmol) of acetic anhydride was added to an anhydrous tetrahydrofuran (10 ml) solution containing 300 mg (0.70 mol) of 3-(4-nitrobenzyloxy)-N-(2-sulfamoylphenyl)benzamide produced in Reference Example 5 and 171 mg (1.40 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 290 mg (yield: 89.8%) of the title compound.

NMR (CDCl$_3$) δ: 2.05 (3 H, s), 5.25 (2 H, s), 7.15–7.19 (1 H, m), 7.23–7.29 (1 H, m), 7.40–7.45 (1 H, m), 7.60–7.71 (5 H, m), 7.96 (1 H, dd, J=8 Hz, 1 Hz), 8.22–8.27 (2 H, m), 8.47 (1 H, br-s), 8.72 (1 H, dd, J=8 Hz, 1 H, z), 10.45 (1 H, br-s)

IR (ν, cm$^{-1}$, KBr): 3384, 3124, 2856, 1714, 1660, 1580, 1532, 1520, 1490, 1476, 1446

EI-MS (m/z, %): 469 (9), 347 (15), 256 (27), 182 (8), 154 (4), 125 (100), 121 (27)

Melting Point: 189–192° C.

Example 21

**N-[2-[3-(4-Nitrobenzyloxy)benzamido]
benzenesulfonyl]hexanamide**

In a stream of nitrogen and at 0° C., 0.11 ml (0.80 mmol) of hexanoyl chloride was added to an anhydrous tetrahydrofuran (10 ml) solution containing 300 mg (0.07 mmol) of 3-(4-nitrobenzyloxy)-N-(2-sulfamoylphenyl)benzamide produced in Reference Example 5 and 171 mg (1.40 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 320 mg (yield: 86.8%) of the title compound.

NMR (CDCl$_3$) δ: 0.81 (3 H, t, J=7 Hz), 1.13–1.28 (4 H, m), 1.49–1.59 (2 H, m), 2.23 (2 H, t, J=7 Hz), 5.25 (2 H, s), 7.15–7.20 (1 H, m), 7.23–7.29 (1 H, m), 7.61–7.71 (5 H, m), 7.97 (1 H, dd, J=8 Hz, 1 Hz), 8.22–8.29 (3 H, m), 8.73 (1 H, dd, J=8 Hz, 1 Hz), 10.48 (1 H, br-s)

IR (ν, cm$^{-1}$, KBr): 3372, 3064, 2956, 2932, 2860, 1714, 1664, 1604, 1586, 1526, 1490, 1472, 1446

EI-MS (m/z, %): 525 (32), 411 (6), 347 (86), 256 (100), 182 (20), 121 (50), 92 (17)

Melting point: 138–141° C.

Example 22

**N-[2-[3-(4-Nitrobenzyloxy)benzamido]
benzenesulfonyl]decanamide**

In a stream of nitrogen and at 0° C., 0.16 ml (0.80 mmol) of decanoyl chloride was added to an anhydrous tetrahydrofuran (10 ml) solution containing 300 mg (0.70 mmol) of 3-(4-nitrobenzyloxy)-N-(2-sulfamoylphenyl)benzamide produced in Reference Example 5 and 171 mg (1.40 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 400 mg (yield: 97.9%) of the title compound.

NMR (CDCl$_3$) δ: 0.86 (3 H, t, J=7 Hz), 1.15–1.30 (12 H, m), 1.48–1.59 (2 H, m), 2.23 (2 H, t, J=7 Hz), 5.25 (2 H, s), 7.15–7.20 (1 H, m), 7.23–7.29 (1 H, m), 7.40–7.46 (1 H, m), 7.61–7.71 (5 H, m), 7.96 (1 H, dd, J=8 Hz, 1 Hz), 8.22 (1 H, br-s), 8.23–8.29 (2 H, m), 8.73 (1 H, dd, J=8 Hz, 1 Hz), 10.48 ( 1 H, br-s)

IR (ν, cm$^{-1}$, KBr): 3376, 3068, 2924, 2852, 1704, 1668, 1606, 1588, 1256, 1490, 1472, 1446

EI-MS (m/z,%): 581 (20), 411 (8), 347 (87), 256 (100), 182 (19), 136 (22)

Melting point: 145–148° C.

Reference Example 6

3-(4-Methoxybenzyloxy)-N-(2-sulfamoylphenyl)benzamide

A benzene (30 ml) solution containing 4.00 g (15.5 mmol) of 3-(4-methoxybenzyloxy)benzoic acid and 3 ml of thionyl chloride was heated under reflux for 2 hours and then the solvent was evaporated under a reduced pressure. The resulting residue was dissolved in methylene chloride (30 ml), this solution was added dropwise under ice-cooling to a pyridine (50 ml) solution containing 2.93 g (17.0 mmol) of 2-aminobenzenesulfonamide, the mixture was stirred at room temperature for 18 hours and then methylene chloride was evaporated under a reduced pressure. The resulting residue was dissolved in ethyl acetate, washed with a 1 N hydrochloric acid aqueous solution, water and saturated brine in that order and dried over anhydrous sodium sulfate, and then the solvent was evaporated under a reduced pressure. The thus obtained residue was purified by a silica gel chromatography to obtain 1.5 g (yield: 31.0%) of the title compound.

NMR (DMSO-d$_6$) δ: 3.76 (3 H, s), 5.11 (2 H, s), 6.96 (2 H, d, J=8 Hz), 7.25–7.30 (1 H, m), 7.33 (1 H, ddd, J=8 Hz, 8 Hz, 1 Hz), 7.73 (2 H, br-s), 7.90 (1 H, dd, J=8 Hz, 1 Hz), 8.48 (1 H, d, J=8 Hz), 10.38 (1 H, br-s)

EI-MS (m/z, %): 412 (m+, 6), 370 (6), 292 (3), 279 (10), 121 (100)

IR (ν, cm$^{-1}$, KRr): 1676, 1612, 1586, 1538, 1518, 1152

Melting point: 164–165° C.

Example 23

N-[2-[3-(4-Methoxybenzyloxy)benzamido]benzenesulfonyl acetamide

In a stream of nitrogen and at 0° C., 0.1 ml (1.10 mmol) of acetic anhydride was added to an anhydrous tetrahydrofuran (10 ml) solution containing 400 mg (1.00 mmol) of 3-(4-methoxybenzyloxy)-N-(2-sulfamoylphenyl)benzamide produced in Reference Example 6 and 237 mg (1.90 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 430 mg (yield: 97.6%) of the title compound.

NMR (CDCl$_3$) δ: 2.04 (3 H, s), 3.82 (3 H, s), 5.07 (2 H, s), 6.90–6.96 (2 H, m), 7.16 (1 H, ddd, J=8 Hz, 2 Hz, 1 Hz), 7.22–7.29 (1 H, m), 7.35–7.43 (3 H, m), 7.58–7.63 (1 H, m), 7.65–7.71 (2 H, m), 7.98 (1 H, dd, J=8 Hz, 1 Hz), 8.27 (1 H, br-s), 8.73 (1 H, dd, J=8 Hz, 1 Hz), 10.34 (1 H, br-s)

IR (ν, cm$^{-1}$, KBr): 3384, 3084, 2872, 1718, 1658, 1612, 1580, 1538, 1518, 1476, 1448

EI-MS (m/z, %): 454 (7), 334 (37), 240 (9), 121 (100)

Melting point: 114–117° C.

Example 24

N-[2-[3-(4-Methoxybenzyloxy)benzamido]benzenesulfonyl]hexanamide

In a stream of nitrogen and at 0° C., 0.15 ml (1.10 mmol) of hexanoyl chloride was added to an anhydrous tetrahydrofuran (10 ml) solution containing 400 mg (1.00 mmol) of 3-(4-methoxybenzyloxy)-N-(2-sulfamoylphenyl)benzamide produced in Reference Example 6 and 237 mg (1.90 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 490 mg (yield: 98.8%) of the title compound.

NMR (CDCl$_3$) δ: 0.81 (3 H, t, J=7 Hz), 1.13–1.27 (4 H, m), 1.48–1.59 (2 H, m), 2.21 (2 H, t, J=7 Hz), 3.82 (3 H, s), 5.07 (2 H, s), 6.90–6.96 (2 H, m), 7.16 (1 H, ddd, J=8 Hz, 2 Hz, 1 Hz), 7.22–7.29 (1 H, m), 7.36–7.44 (3 H, m), 7.60–7.72 (3 H, m), 7.99 (1 H, dd, J=8 Hz, 1 Hz), 8.13 (1 H, br-s), 8.73 (1 H, dd, J=8 Hz, 1 Hz), 10.42 (1 H, br-s)

IR (ν, cm$^{-1}$, KBr): 3392, 3072, 2956, 2932, 2872, 1716, 1658, 1614, 1580, 1538, 1520, 1450, 1412

EI-MS (m/z, %): 510 (2), 390 (2), 178 (6), 154 (2), 121 (100)

Melting point: 154–157° C.

Example 25

N-[2-[3-(4-Methoxybenzyloxy)benzamido]benzenesulfonyl]decanamide

In a stream of nitrogen and at 0° C., 0.22 ml (1.10 mmol) of decanoyl chloride was added to an anhydrous tetrahydrofuran (10 ml) solution containing 400 mg (1.00 mmol) of 3-(4-methoxybenzyloxy)-N-(2-sulfamoylphenyl)benzamide produced in Reference Example 6 and 237 mg (1.90 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 520 mg (yield: 94.6%) of the title compound.

NMR (CDCl$_3$) δ: 0.87 (3 H, t, J=7 Hz), 1.15–1.32 (12 H, m), 1.49–1.60 (2 H, m), 2.22 (2 H, t, J=7 Hz), 3.83 (3 H, s), 5.08 (2 H, s), 6.91–6.96 (2 H, m), 7.17 (1 H, ddd, J=8 Hz, 2 Hz, 1 Hz), 7.23–7.30 (1 H, m), 7.36–7.44 (3 H, m), 7.61–7.73 (3 H, m), 8.00 (1 H, dd, J= 8 Hz, 1 Hz), 8.05 (1 Hz, br-s), 8.74 (1 H, dd, J=8 Hz, 1 Hz), 10.43 (1 H, br-s)

IR (ν, cm$^{-1}$, KBr): 3364, 3036, 2920, 2852, 1704, 1660, 1602, 1586, 1540, 1518, 1490, 1742, 1448, 1440

EI-MS (m/s, %): 566 (3), 275 (9), 211 (8), 121 (100)

Melting point: 148–149° C.

Reference Example 7

3-Cyclohexylmethoxy-N-(2-sulfamoylphenyl)benzamide

A benzene (30 ml) solution containing 3.00 g (12.8 mmol) of 3-cyclohexylmethoxybenzoic acid and 3 ml of thionyl chloride was heated under reflux for 2 hours and then the solvent was evaporated under a reduced pressure. The resulting residue was dissolved in methylene chloride (30 ml), this solution was added dropwise under ice-cooling to a pyridine (50 ml) solution containing 2.43 g (14.1 mmol) of 2-aminobenzenesulfonamide, the mixture was stirred at room temperature for 18 hours and then methylene chloride was evaporated under a reduced pressure. The resulting residue was dissolved in ethyl acetate, washed with a 1 n hydrochloric acid aqueous solution, water and saturated brine in that order and dried over anhydrous sodium sulfate, and then the solvent was evaporated under a reduced pressure. The thus obtained crude crystals were recrystallized from acetonitrile to obtain 2.80 g (yield: 56.0%) of the title compound NMR (CDCl$_3$) δ: 1.00–1.39 (5 H, m), 1.68–1.90 (6 H, m), 3.82 (2 H, d J=7 Hz), 4.95 (2 H, s), 7.10 (1 H, ddd, J=8 Hz, 2 Hz, 1 Hz), 7.25 (1 H, ddd, J=8 Hz, 8 Hz, 1 Hz), 7.38 (1 H, dd, J=8 Hz, 8 Hz), 7.45–7.50 (2 H, m), 7.62 (1 H, ddd, J=8 Hz, 8 Hz, 2 Hz), 7.96 (1 H, dd, J=8 Hz, 2 Hz), 8.53 (1 H, dd, J=8 Hz, 1 Hz), 10.03 (1 H, s)

EI-MS (m/z, %): 388 (m+, 44), 217 (86), 212 (95), 121 (100)

IR (ν, cm$^{-1}$, KBr): 1670, 1580, 1538, 1450, 1158, 1522, 1034

Melting point: 161–162° C.

Example 26

N-[2-(3-Cyclohexylmethoxybenzamido)benzenesulfonyl]acetamide

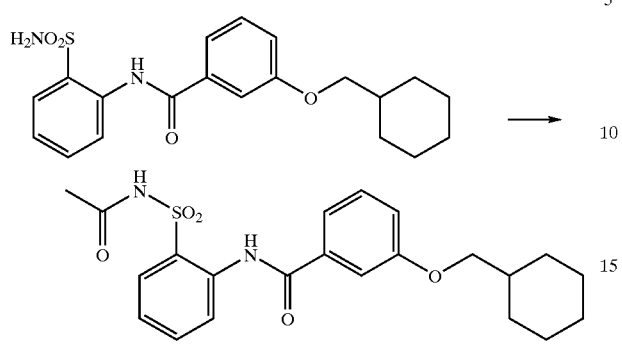

In a stream of nitrogen and at 0° C., 0.11 ml (1.10 mmol) of acetic anhydride was added to an anhydrous tetrahydrofuran (10 ml) solution containing 400 mg (1.00 mmol) of 3-cyclohexylmethoxy-N-(2-sulfamoylphenyl)benzamide produced in Reference Example 7 and 237 mg (1.90 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 430 mg (yield: 96.9%) of the title compound.

NMR (CDCl$_3$) δ: 1.00–1.13 (2 H, m), 1.14–1.37 (3 H, m), 1.66–1.92 (6 H, m), 2.06 (3 H, s), 3.83 (2 H, d, J=6 Hz), 7.07–7.12 (1 H, m), 7.22–7.29 (1 H, m), 7.35–7.42 (1 H, m), 7.54–7.60 (2 H, m), 7.65–7.72 (1 H, m), 7.98 (1 H, dd, J=8 Hz, 1 Hz), 8.30 (1 H, br-s) 8.73 (1 H, dd, J=8 Hz, 1 Hz), 10.34 (1 H, br-s)

IR (ν, cm$^{-1}$, KBr): 3368, 3036, 2932, 2856, 1712, 1662, 1604, 1586, 1542, 1492, 1472, 1450, 1440

EI-MS (m/z %): 430 (37), 308 (12), 275 (14), 183 (8), 121 (100)

Melting point: 164–167° C.

Example 27

N-[2-(3-Cyclohexylmethoxybenzamido)benzenesulfonyl]hexanamide

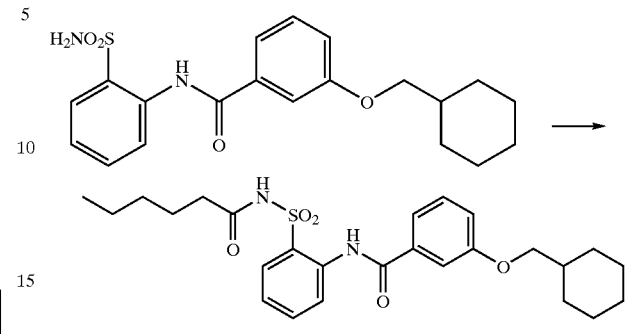

In a stream of nitrogen and at 0° C., 0.16 ml (1.10 mmol) of hexanoyl chloride was added to an anhydrous tetrahydrofuran (10 ml) solution containing 400 mg (1.00 mmol) of 3-cyclohexylmethoxy-N-(2-sulfamoylphenyl)benzamide produced in Reference Example 7 and 237 mg (1.90 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 490 mg (yield: 97.8%) of the title compound.

NMR (CDCl$_3$) δ: 0.84 (3 H, t, J=7 Hz), 1.00–1.13 (2 H, m), 1.14–1.38 (7 H, m), 1.50–1.61 (2 H, m), 1.66–1.92 (6 H, m), 2.23 (2 H, t, J=7 Hz), 3.83 (2 H, d, J=6 Hz), 7.07–7.12 (1 H, m), 7.22–7.29 (1 H, m), 7.36–7.42 (1 H, m), 7.55–7.61 (2 H, m), 7.65–7.71 (1 H, m), 7.99 (1 H, dd, J=8 Hz, 1 Hz), 8.11 (1 H, br-s), 8.73 (1 H, dd, J= 8 Hz, 1 Hz), 10.40 (1 H, br-s)

IR (ν, cm$^{-1}$, KBr): 3380, 3080, 2924, 2856, 1714, 1690, 1664, 1580, 1538, 1476, 1448, 1406

EI-MS (m/z, %): 486 (46), 275 (14), 183 (8), 121 (100)

Melting point: 112–113° C.

Example 28

N-[2-(3-Cyclohexylmethoxybenzamido)benzenesulfonyl]decanamide

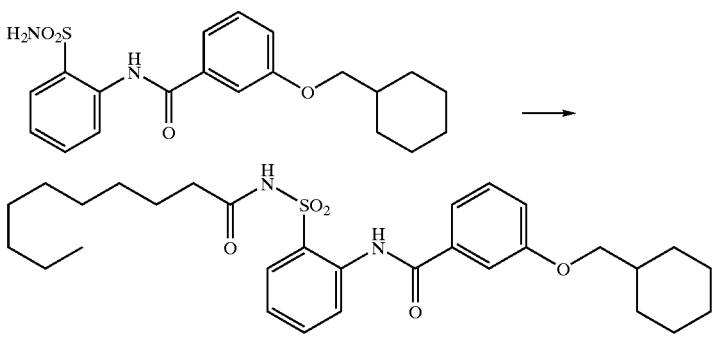

In a stream of nitrogen and at 0° C., 0.24 ml (1.10 mmol) of decanoyl chloride was added to an anhydrous tetrahydrofuran (10 ml) solution containing 400 mg (0.68 mmol) of 3-cyclohexylmethoxy-N-(2-sulfamoylphenyl)benzamide produced in Reference Example 7 and 237 mg (1.90 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 550 mg (yield: 98.4%) of the title compound.

NMR (CDCl$_3$) δ: 0.87 (3 H, t, J=7 Hz), 1.01–1.13 (2 H, m), 1.15–1.37 (15 H, m), 1.49–1.59 (2 H, m), 1.66–1.92 (6 H, m), 2.23 (2 H, t, J=7 Hz), 3.83 (2 H, d, J=6 Hz), 7.07–7.12 (1 H, m), 7.22–7.29 (1 H, m), 7.36–7.42 (1 H, m), 7.55–7.62 (2 H, m), 7.64–7.72 (1 H, m), 7.99 (1 H, dd, J=8 Hz, 1 Hz), 8.08 ( 1 H, br-s), 8.73 (1 H, dd, J= 8 Hz, 1 Hz), 10.40 (1 H, br-s)

IR (ν, cm$^{-1}$, KBr): 3360, 3028, 2924, 2856, 1708, 1658, 1540, 1472, 1448

EI-MS (m/z, %): 542 (29), 275 (9), 183 (6), 121 (100)

Melting point: 124–127° C.

Example 29

N-[2-[3-(4-t-Butylbenzyloxy)benzamido]benzenesulfonyl]acetamide

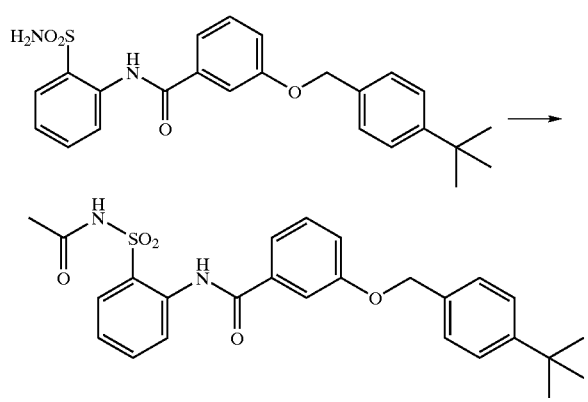

In a stream of nitrogen and at 0° C., 0.11 ml (1.10 mmol) of acetic anhydride was added to an anhydrous tetrahydrofuran (10 ml) solution containing 438 mg (1.00 mmol) of 3-(4-t-butylbenzyloxy)-N-(2-sulfamoylphenyl)benzamide produced in Reference Example 2 and 249 mg (2.00 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 456 mg (yield: 96.0%) of the title compound.

NMR (CDCl$_3$) δ: 1.29 (9 H, s), 1.93 (3 H, s), 5.15 (2 H, s), 7.17 (1 H, ddd, J=8 Hz, 2 Hz, 1 Hz), 7.22–7.29 (1 H, m), 7.38–7.44 (5 H, m), 7.60–7.63 (1 H, m), 7.65–7.71 (2 H, m), 7.99 (1 H, dd, J=8 Hz, 2 Hz), 8.73 (1 H, dd, J=8 Hz, 1 Hz), 7.56 (1 H, d, J=7 Hz), 7.60 (1 H, s), 7.72 (1 H, m), 7.91 (1 H, d, J=8 Hz), 8.40 (1 H, d, J=8 Hz), 10.40 (1 H, br-s)

EI-MS (m/z, %): 480 (m+, 26), 422 (1), 267 (4), 147 (100)

IR (ν, cm$^{-1}$, KBr): 3384, 2956, 2868, 1714, 1658, 1580, 1538

Melting point: 190–191° C.

Example 30

N-[2-[3-(4-t-Butylbenzyloxy)benzamido]benzenesulfonyl]hexanamide

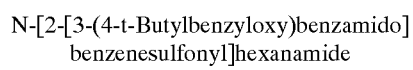

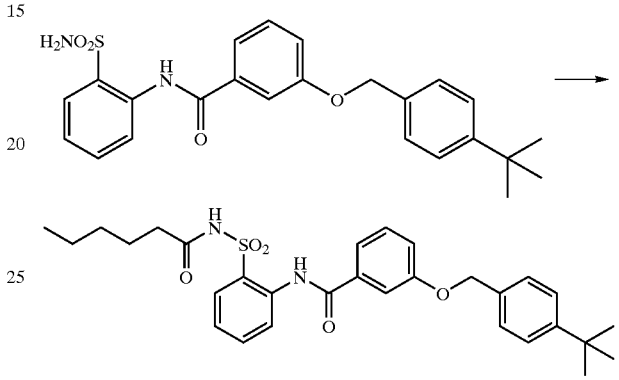

In a stream of nitrogen and at 0° C., 0.16 ml (1.10 mmol) of hexanoyl chloride was added to an anhydrous tetrahydrofuran (10 ml) solution containing 438 mg (1.00 mmol) of 3-(4-t-butylbenzyloxy)-N-(2-sulfamoylphenyl)benzamide produced in Reference Example 2 and 249 mg (2.00 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 488 mg (yield: 91.0%) of the title compound.

NMR (CDCl$_3$) δ: 0.82 (3 H, t, J=7 Hz), 1.21 (4 H, m), 1.33 (9 H, s), 1.54 (2 H, m), 2.23 ( 2 H, t, J=7 Hz), 5.10 (2 H, s), 7.18 ( 1 H, ddd, J=8 Hz, 2 Hz, 1 Hz), 7.26 (1 H, ddd, J=8 Hz, 8 Hz, 2 Hz), 7.38–7.44 (5 H, m), 7.62 (1 H, d, J=8 Hz), 7.65–7.74 (2 H, m), 7.96 (1 H, br-s), 8.00 (1 H, dd, J=8 Hz, 2 Hz), 8.74 (1 H, dd, J=8 Hz, 1 Hz), 10.43 (1 H, br-s)

EI-MS (m/s, %): 536 (m+, 49), 422 (4), 267 (14), 147 (100), 91 (21), 71 (4)

IR (ν, cm$^{-1}$, KBr): 3368, 2960, 2868, 1702, 1662, 1586, 1538

Melting point: 163–164° C.

Example 31

N-[2-[3-(4-t-Buylbenzyloxy)benzamido]benzenesulfonyl]decanamide

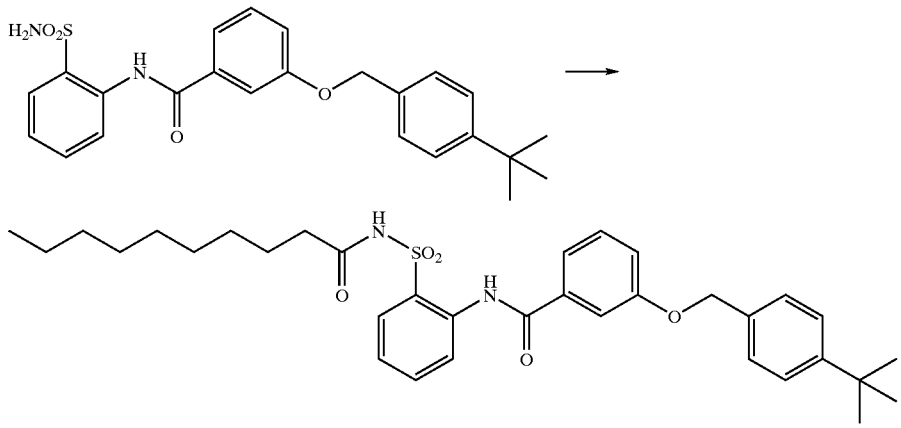

In a stream of nitrogen and at 0° C., 0.24 ml (1.10 mmol) of decanoyl chloride was added to an anhydrous tetrahydrofuan (10 ml) solution containing 438 mg (1.00 mmol) of 3-(4-t-butylbenzyloxy)-N-(2-sulfamoylphenyl)benzamide produced in Reference Example 2 and 249 mg (2.00 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 535 mg (yield: 99.0%) of the title compound.

NMR (CDCl$_3$) δ: 0.86 (3 H, t, J=7 Hz), 1.22 (14 H, m), 1.33 (9 H, s), 2.23 (2 H, t, J=7 Hz), 5.10 (2 H, s), 7.18 (1 H, ddd, J=8 Hz, 2 Hz, 1 Hz), 7.26 (1 H, ddd, J=8 Hz, 8 Hz, 2 Hz), 7.38–7.44 (5 H, m), 7.62 (1 H, d, J=8 Hz), 7.65–7.74 (2 H, m), 7.94 (1 H, br-s), 8.00 (1 H, dd, J=8 Hz, 2 Hz), 8.74 (1 H, dd, J=8 Hz, 1 Hz), 10.43 (1 H, br-s)

EI-MS (m/z, %): 592 (m+, 30), 422 (3), 267 (16), 147 (100)

IR (ν, cm$^{-1}$, KBr): 3368, 3064, 3036, 2960, 2924, 2856, 1704, 1660, 1586, 1540

Melting point: 132–133° C.

Reference Example 8

3-(4-Trifluoromethylbenzyloxy)-N-(2-sulfamoylphenyl)benzamide

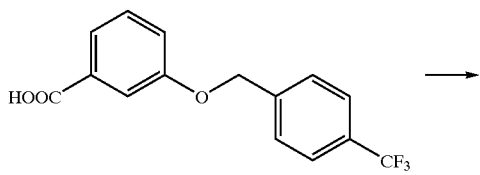

→

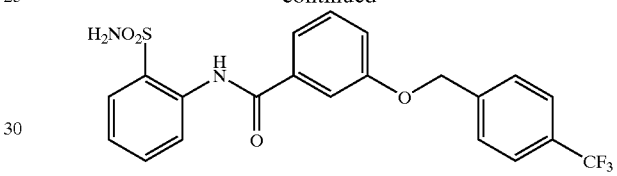

A benzene (30 ml) solution containing 4.00 g (14.1 mmol) of 3-(4-trifluoromethylbenzyloxy)benzoic acid and 3 ml of thionyl chloride was heated under reflux for 2 hours and then the solvent was evaporated under a reduced pressure. The resulting residue was dissolved in methylene chloride (30 ml), this solution was added dropwise under ice-cooling to a pyridine (50 ml) solution containing 2.66 g (15.4 mmol) of 2-aminobenzenesulfonamide, the mixture was stirred at room temperature for 18 hours and then methylene chloride was evaporated under a reduced pressure. The resulting residue was dissolved in ethyl acetate, washed with a 1 N hydrochloric acid aqueous solution, water and saturated brine in that order and dried over anhydrous sodium sulfate, and then the solvent was evaporated under a reduced pressure. The thus obtained crude crystals were washed with methanol to obtain 5.10 g (yield: 80.0%) of the title compound.

NMR (CDCl-d$_6$) δ: 5.33 (2 H, s), 7.29–7.36 (2 H, m), 7.50–7.58 (3 H, m), 7.65 (1 H, ddd, J=8 Hz, 8 Hz, 2 Hz), 7.69 (2 H, d, J=8 Hz), 7.78 (2 H, d, J=8 Hz), 7.90 (1 H, dd, J=8 Hz, 2 Hz), 8.47 (1 H, dd, J=8 Hz, 1 Hz)

EI-MS (m/z, %): 450 (m+, 68), 371 (100), 279 (100), 159 (100)

IR (ν, cm$^{-1}$, KBr): 1678, 1586, 1538, 1326, 1066

Melting point: 169–170° C.

Example 32

N-([2-[3-(4-Trifluoromethylbenzyloxy)benzamido]benzenesulfonyl]acetamide

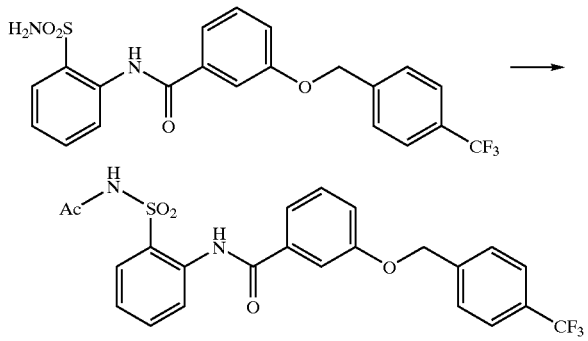

In a stream of nitrogen and at 0° C., 0.11 ml (1.10 mmol) of acetic anhydride was added to an anhydrous tetrahydrofuran (10 ml) solution containing 451 mg (1.00 mmol) of 3-(4-trifluoromethylbenzyloxy)-N-(2-sulfamoylphenyl) benzamide produced in Reference Example 8 and 249 mg (2.00 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 476 mg (yield: 96.7%) of the title compound.

NMR (CDCl$_3$) δ: 2.05 (3 H, s), 5.21 (2 H, s), 7.16 (1 H, ddd, J=8 Hz, 2 Hz, 1 Hz), 7.26 (1 H, ddd, J=8 Hz, 8 Hz, 2 Hz), 7.42 (1 H, dd, J=8 Hz, 8 Hz), 7.57 (2 H, d, J=8 Hz), 7.65–7.74 (5 H, m), 7.96 (1 H, dd, J=8 Hz, 2 Hz), 8.30 (1 H, br-s), 8.73 (1 H, dd, J=8 Hz, 1 Hz), 10.44 (1 H, br-s)

EI-MS (m/z, %): 492 (m+, 3), 370 (35), 279 (92), 159 (100), 121 (22)

IR (ν, cm$^{-1}$, KBr): 3372, 3124, 2880, 1724, 1678, 1614, 1588, 1546

Melting point: 164–165° C.

Example 33

N-[2-[3-(4-Trifluoromethylbenzyloxy)benzamido]benzenesulfonyl]hexanamide

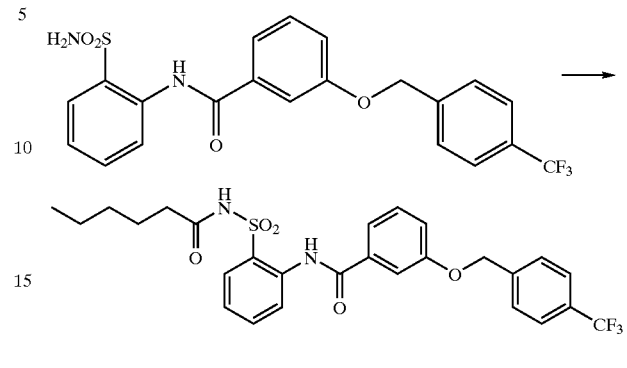

In a stream of nitrogen and at 0° C. 0.16 ml (1.10 mmol) of hexanoyl chloride was added to an anhydrous tetrahydrofuran (10 ml) solution containing 451 mg (1.00 mmol) of 3-(4-trifluoromethylbenzyloxy)-N-(2-sulfamoylphenyl) benzamide produced in Reference Example 8 and 249 mg (2.00 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 439 mg (yield: 80.0%) of the title compound.

NMR (CDCl$_3$) δ: 0.82 (3 H, t, J=7 Hz), 1.21 (4 H, m), 1.55 (2 H, m), 2.23 (2 H, t, J=7 Hz), 5.21 (2 H, s), 7.17 (1 H, ddd, J=8 Hz, 2 Hz, 1 Hz), 7.26 (1 H, ddd, J=8 Hz, 8 Hz, 2 Hz), 7.43 (1 H, dd, J=8 Hz, 8 Hz), 7.57 (2 H, d, J=8 Hz), 7.63–7.72 (5 H, m), 7.98 (1 H, dd, J=8 Hz, 2 Hz), 8.02 (1 H, br-s), 8.74 (1 H, dd, J=8 Hz, 1 Hz), 10.46 (1 H, br-s)

EI-MS (m/z, %): 548 (m+, 25), 370 (50), 279 (100), 159 (96), 121 (25)

IR (ν, cm$^{-1}$, KBr): 3380, 3080, 2960, 2932, 2872, 1708, 1660, 1584, 1540

Melting point: 142–143° C.

Example 34

N-[2-[3-(4-Trifluoromethylbenzyloxy)benzamido]benzenesulfonyl]decanamide

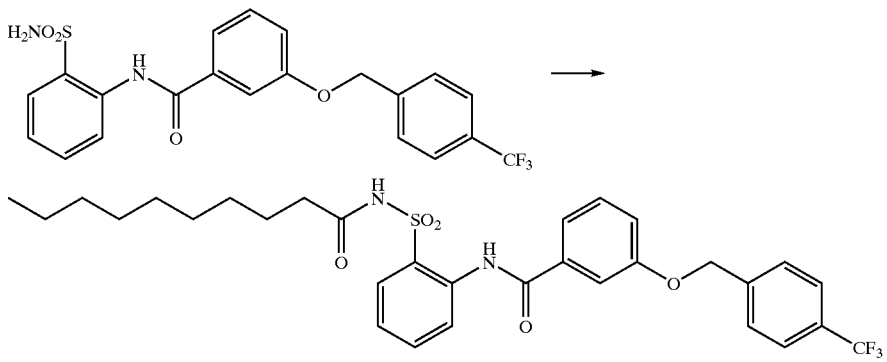

In a stream of nitrogen and at 0° C., 0.24 ml (1.10 mmol) of decanoyl chloride was added to an anhydrous tetrahydrofuran (10 ml) solution containing 451 mg (1.00 mmol) of 3-(4-trifluoromethylbenzyloxy)-N-(2-sulfamoylphenyl)benzamide produced in Reference Example 8 and 249 mg (2.00 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 512 mg (yield: 84.6%) of the title compound.

NMR (CDCl$_3$) δ: 0.86 (3 H, t, J=7 Hz), 1.16–1.28 (12 H, m), 1.53 (2 H, m), 2.23 (2 H, t, J=7 Hz), 5.21 (2 H, s), 7.16 (1 H, ddd, J=8 Hz, 2 Hz, 1 Hz), 7.26 (1 H, ddd, J=8 Hz, 8 Hz, 2 Hz), 7.43 (1 H, dd, J=8 Hz, 8 Hz), 7.58 (2 H, d, J=8 Hz), 7.63–7.73 (5 H, m), 7.97 (1 H, dd, J=8 Hz, 2 Hz), 8.25 (1 H, br-s), 8.73 (1 H, dd, J=8 Hz, 1 Hz), 10.47 (1 H, br-s)

EI-MS (m/z, %): 604 (m+, 28), 370 (57), 279 (100), 159 (82)

IR (ν, cm$^{-1}$, KBr): 3372, 3036, 2924, 282, 2788, 1702, 1666, 1606, 1588, 1544

Melting point: 164° C.

Reference Example 9

3-Heptyloxy-N-(2-sulfamoylphenyl)benzamide

A benzene (30 ml) solution containing 3 g (12.5 mmol) of 3-heptyloxybenzoic acid and 3 ml of thionyl chloride was heated under reflux for 2 hours and then the solvent was evaporated under a reduced pressure. The resulting residue was dissolved in methylene chloride (30 ml), this solution was added dropwise under ice-cooling to a pyridine (50 ml) solution containing 2.50 g (14.5 mmol) of 2-aminobenzenesulfonamide, the mixture was stirred at room temperature for 18 hours and then methylene chloride was evaporated under a reduced pressure. The resulting residue was dissolved in ethyl acetate, washed with a 1 N hydrochloric acid aqueous solution, water and saturated brine in that order and dried over anhydrous sodium sulfate, and then the solvent was evaporated under a reduced pressure. The thus obtained crude crystals were recrystallized from acetonitrile to obtain 3.00 g (yield: 60.0%) of the title compound. NMR (DMS-d$_6$) δ: 0.87 (3 H, t, J=7 Hz), 1.22–1.50 (8 H, m), 1.70–1.80 (2 H, M), 4.41 (2 H, t, J=7 Hz), 7.17–7.23 (1 H, m), 7.33 (1 H, ddd, J=8 Hz, 8 Hz, 2 Hz), 7.77 (2 H, s), 7.90 (1 H, dd, J=8 Hz, 2 Hz), 8.48 (1 H, d, J=8 Hz), 10.38 (1 H, s)

EI-MS (m/z, %): 390 (m+, 82), 311 (43), 310 (100), 219 (100)

IR (ν, cm$^{-1}$, KBr): 1674, 1612, 1586, 1544, 1336, 1140

Melting point: 112–113° C.

Example 35

N-[2-(3-Heptyloxybenzamido)benzenesulfonyl]acetamide

In a stream of nitrogen and at 0° C., 0.11 ml (1.10 mmol) of acetic anhydride was added to an anhydrous tetrahydrofuran (10 ml) solution containing 391 mg (1.00 mmol) of 3-heptyloxy-N-(2-sulfamoylphenyl)benzamdie produced in Reference Example 9 and 249 mg (2.00 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 411 mg (yield: 95.0%) of the title compound.

NMR (CDCl-d$_6$) δ: 0.87 (3 H, t, J=7 Hz), 1.35 (8 H, m), 1.68 (3 H, s), 1.75 (2 H, m), 4.04 (2 H, t, J=6 Hz), 7.10–7.15 (2 H, m), 7.38 –7.46 (2 H, m), 7.57–7.64 (2 H, m), 7.75 (1 H, dd, J=8 Hz, 2 Hz), 8.34 (1 H, dd, J=8 Hz, 1 Hz), 11.51 (1 H, s)

EI-MS (m/z, %): 432 (m+, 7), 310 (31), 219 (100), 121 (12)

IR (ν, cm$^{-1}$, KBr): 2928, 2856, 1684, 1586, 1552, 1494

Melting point: 194–195° C.

Example 36

N-[2-(3-Heptyloxybenzamido)benzenesulfonyl]hexanamide

In a stream of nitrogen and at 0° C., 0.16 ml (1.10 mmol) of hexanoyl chloride was added to an anhydrous tetrahydrofuran (10 ml) solution containing 390 mg (1.00 mmol) of 3-heptyloxy-N-(2-sulfamoylphenyl)benzamide produced in Reference Example 9 and 249 mg (2.00 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 412 mg (yield: 84.4%) of the title compound.

NMR (DMSO-$d_6$) δ: 0.76 (3 H, t, J=7 Hz), 0.87 (3 H, d, J=7 Hz), 1.12 (4 H, m), 1.26–1.47 (10 H, m), 1.75 (2 H, m), 1.92 (2 H, m), 4.03 (2 H t, J=6Hz), 7.10–7.15 (2H, m), 7.38–7.46 (2H, m), 7.58 (1H, ddd, J=8Hz, 2Hz, 1Hz), 7.65 (1H, dd, J=2Hz, 1Hz), 7.74 (1H, dd, J=8Hz, 2Hz), 8.34 (1H, dd, J=8Hz, 1Hz), 11.46 (1H, s)

EI-MS (m/z, %): 488 (m+, 2), 310 (12), 219 (69), 196 (100), 121 (40)

IR (v, $cm^{-1}$, KBr): 2928, 2860, 1684, 1594, 1552, 1494

Melting point: 200–201° C.

Example 37

N-[2-(3-Heptyloxybenzamido]benzenesulfonyl] decanimide

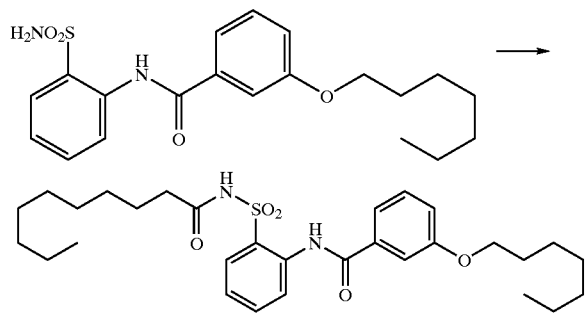

In a stream of nitrogen and at 0° C., 0.24 ml (1.10 mmol) of decanoyl chloride was added to an anhydrous tetrahydrofuran (10 ml) solution containing 390 mg (1.00 mmol) of 3-heptyloxy-N-(2-sulfamoylphenyl)benzamide produced in Reference Example 9 and 249 mg (2.00 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 495 mg (yield: 91.0%) of the title compound.

NMR (DMSO-$d_6$) δ: 0.84 (6H, m), 1.04–1.47 (2H, m), 1.75 (2H, m), 1.91 (2H, t, J=7Hz), 4.04 (2H, t, J=6Hz), 7.10–7.15 (2H, m), 7.38–7.46 (2H, m), 7.58 (1H, d, J=8Hz), 7.66 (1H, dd, J=2Hz, 1Hz), 7.74 (1H, dd, J=8Hz, 2Hz), 8.34 (1H, dd, J=8Hz, 1Hz), 11.43 (1H, s)

EI-MS (m/z, %): 544 (m+, 2), 310 (21), 219 (100), 121 (36)

IR (V, $cm^{-1}$, KBr): 2928, 2856, 1684, 1592, 1552, 1494

Melting point: 172–174° C.

Reference Example 10

4-Phenylethynyl-N-(2-sulfamoylphenyl)benzamide

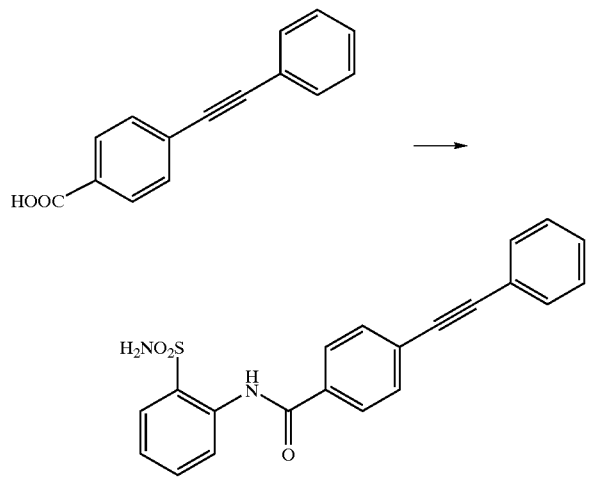

A benzene (30 ml) solution containing 3.00 g (13.5 mmol) of 4-phenylethynylbenzoic acid and 2 ml of thionyl chloride was heated under reflux for 2 hours and then the solvent was evaporated under a reduced pressure. The resulting residue was dissolved in methylene chloride (30 ml), this solution was added dropwise under ice-cooling to a pyridine (50 ml) solution containing 2.32 g (13.50 mmol) of 2-aminobenzenesulfonamide, the mixture was stirred at room temperature for 18 hours and then methylene chloride was evaporated under a reduced pressure. The resulting residue was dissolved in ethyl acetate, washed with a 1 N hydrochloric acid aqueous solution, water and saturated brine in that order and dried over anhydrous sodium sulfate, and then the solvent was evaporated under a reduced pressure. The resulting residue was recrystallized from ethyl acetate-hexane to obtain 4.00 g (yield: 78.7%) of the title compound.

NMR (DMSO-$d_6$) δ: 7.34–7.39 (1H, m), 7.44–7.50 (3H, m), 7.58–7.70 (3H, m), 7.77 (2H, d, J=8Hz), 7.92 (1H, dd, J=8Hz, 1Hz), 7.97 (2H, d, J=8Hz), 8.44 (1H, d, J=8Hz), 10.50 (1H, br-s)

Example 38

N-[2-(4-Phenylethynylbenzamido)benzenesulfonyl] acetamide

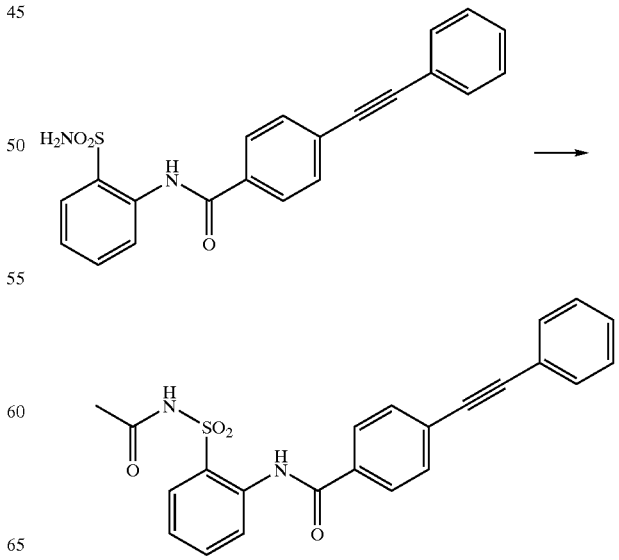

In a stream of nitrogen and at 0° C., 0.15 ml (1.60 mmol) of acetic anhydride was added to an anhydrous tetrahydrofuran (10 ml) solution containing 500 mg (1.30 mmol) of 4-phenylethynyl-N-(2-sulfamoylphenyl)benzamide produced in Reference Example 10 and 320 mg (2.60 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was recrystallized from methanol to obtain 430 mg (yield: 77.6%) of the title compound.

NMR (CDCl$_3$) δ: 2.07 (3H, s), 7.24–7.30 (1H, m), 7.34–7.40 (3H, m), 7.53–7.60 (2H, m), 7.65 (2H, d, J=8Hz), 7.66–7.72 (1H, m), 7.99 (1H, dd, J=8, 1Hz), 8.03 (2H, d, J=8Hz), 8.42 (1H, dd, J=8, 1Hz), 10.47 (1H, s)

IR (v, cm$^{-1}$, KBr): 3384, 1712, 1658, 1588, 1538, 1342, 1172, 764

EI-MS (m/z, %): 418 (m+, 25), 296 (13), 267 (3), 205 (100), 176 (22)

Melting point: 214–215° C.

Example 39

N-[2-(4-Phenylethynylbenzamido)benzenesulfonyl]acetamide

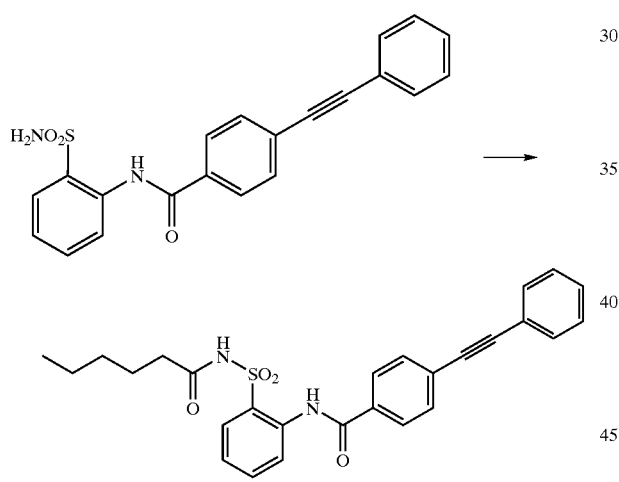

In a stream of nitrogen and at 0° C., 0.20 ml (1.46 mmol) of hexanoyl chloride was added to an anhydrous tetrahydrofuran (10 ml) solution containing 500 mg (1.30 mmol) of 4-phenylethynyl-N-(2-sulfamoylphenyl)benzamide produced in Reference Example 10 and 320 mg (2.60 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 460 mg (yield: 74.6%) of the title compound.

NMR (CDCl$_3$) δ: 0.84 (3H, t, J=7Hz), 1.16–1.30 (4H, m), 1.52–1.60 (2H, m), 2.24 (2H, t, J=7Hz), 7.24–7.29 (1H, m), 7.35–7.40 (3H, m), 7.54–7.59 (2H, m), 7.65 (2H, d, J=8Hz), 7.66–7.72 (1H, m), 7.98 (1H, dd, J=8Hz, 1Hz), 8.04 (2H, d, J=8Hz), 8.16 (1H, br-s), 8.74 (1H, dd, J=8Hz, 1Hz), 10.49 (1H, s)

IR (v, cm$^{-1}$, KBr): 3372, 2956, 1712, 1662, 1590, 1440, 1340, 1142, 766

EI-MS (m/z, %): 474 (m+, 22), 376 (3), 296 (16), 267 (3), 205 (100), 176 (17)

Melting point: 175–176° C.

Example 40

N-[2-(4-Phenylethynylbenzamido)benzenesulfonyl]decanamide

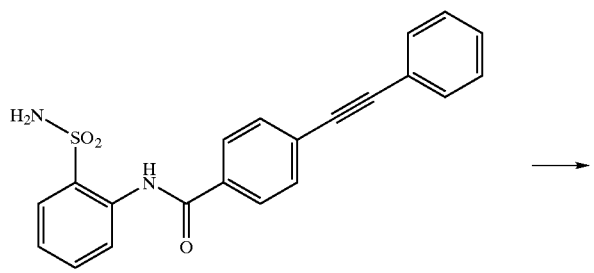

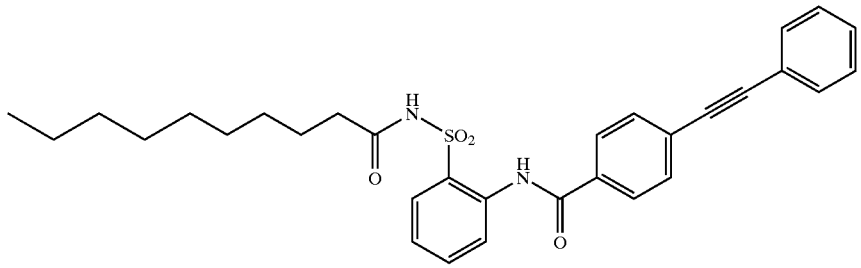

In a stream of nitrogen, 0.30 ml (1.46 mmol) of decanoyl chloride was added to an anhydrous tetrahydrofuran (10 ml) solution containing 500 mg (1.30 mmol) of 4-phenylethynyl-N-(2-sulfamoylphenyl)benzamide produced in Reference Example 10 and 320 mg (2.60 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 540 mg (yield: 76.4%) of the title compound.

NMR (CDCl$_3$) δ: 0.86 (3H, t, J=7Hz), 1.18–1.32 (12H, m), 1.50–1.62 (4H, m), 2.24 (2H, t, J=7Hz), 7.24–7.29 (1H, m), 7.34–7.40 (3H, m), 7.54–7.58 (2H, m), 7.65 (2H, d, J=8Hz), 7.66–7.72 (1H, m), 7.98 (1H, dd, J=8Hz, 1Hz), 8.04 (2H, d, J=8Hz), 8.16 (1H, br-s), 8.74 (1H, dd, J=8Hz, 1Hz), 10.49 (1H, s)

IR (v, cm$^{-1}$, KBr): 3368, 2956, 1712, 1660, 1588, 1540, 1442, 1340, 1144, 764

EI-MS (m/z, %): 530 (m+, 21), 376 (5), 296 (18), 267 (3), 205 (100), 176 (14)

Melting point: 155–156° C.

Example 41

N-[2-(4-Phenylethynylbenzamido)benzenesulfonyl]pivalamide furan (10 ml) solution containing 400 mg (1.06 mmol) of 4-phenylethynyl-N-(2-sulfamoylphenyl)benzamide produced in Reference Example 10 and 260 mg (2.12 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 360 mg (yield: 73.0%) of the title compound.

NMR (CDCl$_3$) δ: 1.15 (9H, s), 7.27 (1H, ddd, J=8Hz, 8Hz, 2Hz), 7.32–7.42 (3H, m), 7.52–7.60 (2H, m), 7.65–7.72 (3H, m), 7.97 (1H, dd, J=8Hz, 2Hz), 8.04 (2H, dd, J=9Hz, 2Hz), 8.23 (1H, br-s), 8.73 (1H, dd, J=8Hz, 2Hz), 10.47 (1H, s)

IR (v, cm$^{-1}$, KBr): 2220, 1712, 1680, 1606, 1588, 1532, 1474, 1440, 1256, 1108

EI-MS (m/z, %): 460 (m+, 55), 296 (34), 205 (100), 176 (30)

Melting point: 236–237° C.

Example 42

3-Methyl-N-[2-(4-phenylethynylbenzamido)benzenesulfonyl]-2-butenamide

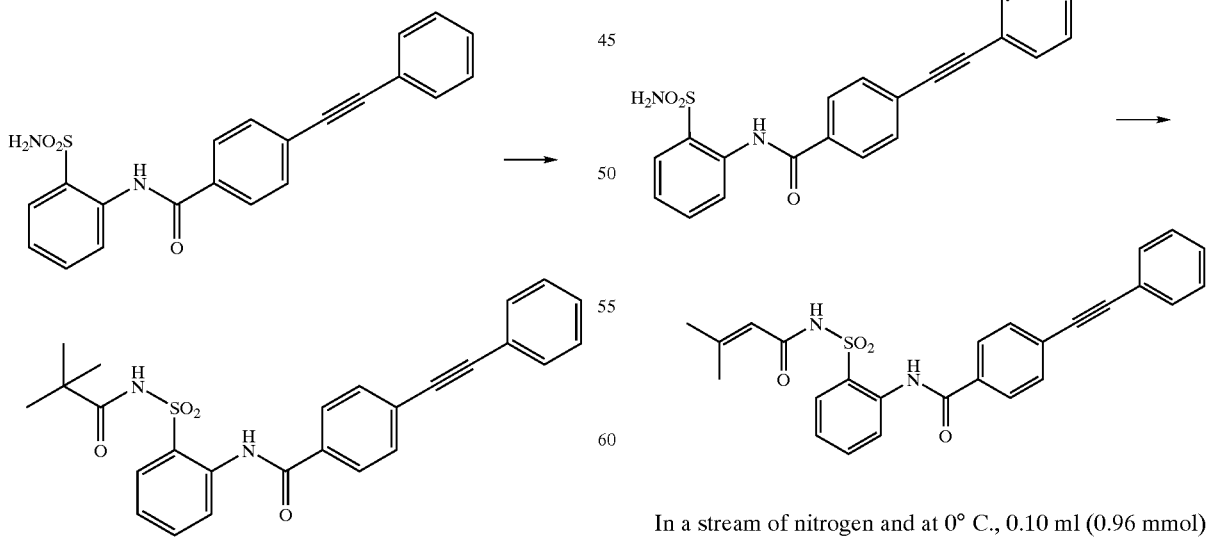

In a stream of nitrogen and at 0° C., 0.16 ml (1.31 mmol) of pivaloyl chloride was added to an anhydrous tetrahydro- In a stream of nitrogen and at 0° C., 0.10 ml (0.96 mmol) of 3,3-dimethylacryloyl chloride was added to an anhydrous tetrahydrofuran (10 ml) solution containing 300 mg (0.80 mmol) of 4-phenylethynyl-N-(2-sulfamoylphenyl)benzamide produced in Reference Example 10 and 195 mg (1.60 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel column chromatography to obtain 183 mg (yield: 50.0%) of the title compound.

NMR (CDCl$_3$) δ: 1.55 (3H, s), 1.88 (3H, s), 5.51 (1H, s), 7.27 (1H, ddd, J=8Hz, 8Hz, 2Hz), 7.37–7.41 (3H, m), 7.55–7.59 (2H, m), 7.64–7.60 (3H, m), 7.93 (1H, br-s), 8.00 (1H, dd, J=8Hz, 2Hz), 8.07 (2H, dd, J=8Hz, 2Hz), 8.72 (1H, dd, J=8Hz, 2Hz), 10.60 (1H, s)

IR (v, cm$^{-1}$, KBr): 2216, 1698, 1684, 1658, 1644, 1608, 1442, 1334, 1300, 1118

EI-MS (m/z, %): 458 (m+, 65), 376 (15), 296 (39), 205 (100), 176 (52)

Melting point: 187–188° C.

Example 43 trans-N-[2-(4-Phenylethynylbenzamido)benzenesulfonyl]-2,4-hexadienamide

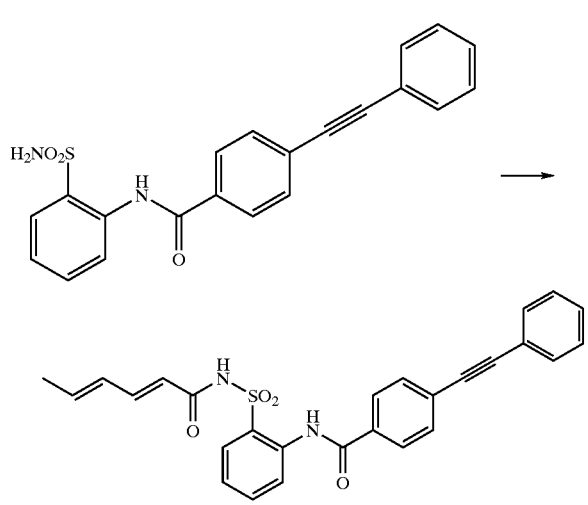

In a stream of nitrogen and at 0° C., 0.10 ml (0.96 mmol) of 2,4-hexadienoyl chloride was added to an anhydrous tetrahydrofuran (10 ml) solution containing 300 mg (0.80 mmol) of 4-phenylethynyl-N-(2-sulfamoylphenyl)benzamide produced in Reference Example 10 and 195 mg (1.60 mmol) of 4-dimethylaminopyridine, the mixture was stirred at room temperature for 1 hour and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The thus formed crude crystals were recrystallized from methanol to obtain 180 mg (yield: 48.0%) of the title compound.

NMR (CDCl$_3$) δ: 1.86 (3H, d, J=6Hz), 5.65 (1H, d, J=15Hz), 6.10–6.26 (2H, m), 7.22–7.30 (2H, m), 7.34–7.40 (3H, m), 7.54–7.59 (2H, m), 7.64–7.70 (3H, m), 7.99 (1H, dd, J=8Hz, 2Hz), 8.02 (1H, br-s), 8.06–8.10 (2H, m), 8.75 (1H, dd, J=8Hz, 2Hz), 10.61 (1H, s)

IR (v, cm$^{-1}$, KBr): 2220, 1698, 1668, 1640, 1590, 1538, 1474, 1440, 1346, 1160

EI-MS (m/z, %): 470 (m+, 39), 360 (24), 296 (40), 205 (100), 176 (100), 151 (42)

Melting point: 208–209° C.

Example 44 trans-N-[2-(4-Phenylethynylbenzamido)benzenesulfonyl]-3-hexenamide

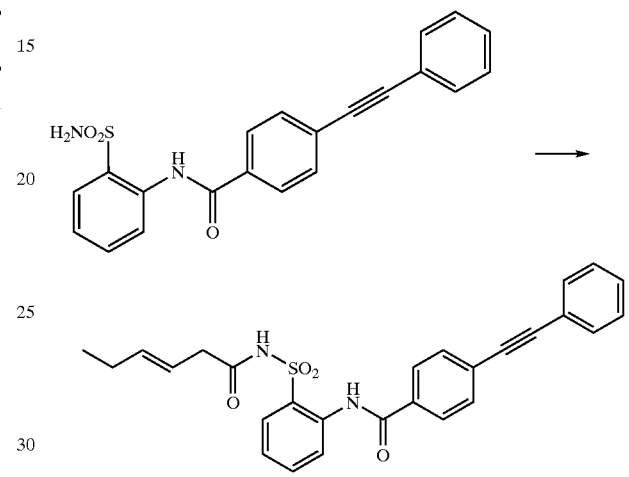

In a stream of nitrogen and at 0° C., 249 mg (1.30 mmol) of tosylic chloride was added to an anhydrous tetrahydrofuran (10 ml) solution containing 149 mg (1.30 mmol) of 3-hexenoic acid and 532 mg (4.35 mmol ) of 4-dimethylaminopyridine, and the mixture was stirred for 1 hour. Next, this was mixed with 300 mg (0.80 mmol) of 4-phenylethynyl-N-(2-sulfamoylphenyl)benzamide produced in Reference Example 10 and stirred at room temperature for 1 hour, and then the solvent was evaporated under a reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel chromatography to obtain 250 mg (yield: 65.0%) of the title compound.

NMR (CDCl$_3$) δ: 0.97 (3H, t, J=7Hz), 2.00–2.10 (2H, m), 2.98 (2H, d, J=7Hz), 5.34–5.42 (1H, m), 5.65–5.72 (1H, m), 7.27 (1H, ddd, J=8Hz, 8Hz, 2Hz), 7.35–7.41 (3H, m), 7.53–7.59 (2H, m), 7.63–7.72 (3H, m), 7.97 (1H, dd, J=8Hz, 2Hz), 8.04 (2H, dd, J=8Hz, 2Hz), 8.23 (1H, br-s), 8.73 (1H, dd, J=8Hz, 2Hz), 10.45 (1H, s)

IR (v, cm$^{-1}$, KBr): 2220, 1718, 1660, 1602, 1590, 1538, 1444, 1430, 1340, 1128

EI-MS (m/z, %): 470 (m+, 71), 360 (19), 296 (39), 205 (100), 176 (76), 151 (32)

Melting point: 185.5–186.5° C.

Example 45

3-Benzyloxy-N-[2-[(phenyloxycarbonylamino)sulfonyl]phenyl]benzamide

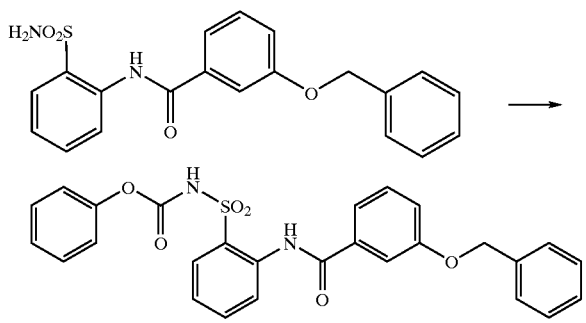

In a stream of nitrogen and at 0° C., 0.36 ml (2.87 mmol) of phenyl chlorocarbonate was added to an anhydrous tetrahydrofuran (10 ml) solution containing 1 g (2.60 mmol) of 3-benzyloxy-N-(2-sulfamoylphenyl)benzamide produced in Reference Example 1 and 702 mg (5.75 mmol) of 4-dimethylaminopyridine, the mixture was stirred at room temperature for 1 hour and then the solvent was evaporated under reduced pressure. The resulting residue was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was recrystallized from acetonitrile to obtain 1.00 g (yield: 77.0%) of the title compound.

NMR (CDCl$_3$) δ: 5.10 (2H, s), 6.98–7.01 (2H, m), 7.14–7.21 (2H, m), 7.24–7.32 (4H, m), 7.33–7.46 (5H, m), 7.55 (1H, ddd, J=8Hz, 2Hz, 1Hz), 7.60 (1H, dd, J=2Hz, 1Hz), 7.71 (1H, ddd, J=8, 8, 2Hz), 7.80 (1H, br-s), 8.07 (1H, dd, J=8Hz, 2Hz), 8.78 (1H, dd, J=8Hz, 1Hz), 10.33 (1H, s)

IR (v, cm$^{-1}$, KBr): 1762, 1664, 1582, 1534, 1462, 1442, 1360, 1164 FAB-MS (neg: m/z, %): 501 ([M-H]+27), 407 (38), 381 (100)

Melting point: 163–164° C.

Example 46

3-Benzyloxy-N-[2-[[(butylamino)carbonylamino]sulfonyl]phenyl]benzamide

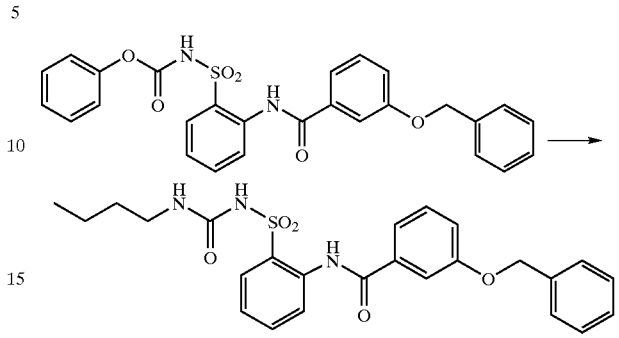

A benzene (10 ml) solution containing 200 mg (0.40 mmol) of 3-benzyloxy-N-[2-[(phenyloxycarbonylamino)sulfonyl]phenyl]benzamide produced in Example 45 and 0.09 ml (0.88 mmol) of butylamine was heated under reflux for 2 hours. The reaction mixture was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was recrystallized from acetonitrile to obtain 130 mg (yield: 68.0%) of the title compound.

NMR (CDCl$_3$) δ: 0.83 (3H, t, J=7Hz), 1.14–1.29 (2H, m), 1.31–1.37 (2H, m), 2.98 (2H, dt, J=7, 7Hz), 5.14 (2H, s), 6.11 (1H, br-s), 7.16 (1H, ddd, J=8Hz, 2Hz, 1Hz), 7.23 (1H, ddd, J=8Hz, 8Hz, 1Hz), 7.31–7.42 (5H, m), 7.45 (2H, dd, J=8, 2Hz), 7.53 (1H, d, J=8Hz), 7.63–7.69 (2H, m), 7.85 (1H, dd, J=8Hz, 2Hz), 8.38 (1H, br-s), 8.70 (1H, dd, J=8Hz, J=1Hz), 10.13 (1H, s)

IR (v, cm$^{-1}$, KBr): 1698, 1650, 1580, 1538, 1484, 1450, 1330, 1166 FAB-MS (neg: m/z, %): 480 ([M-H]+100), 381 (27)

Melting point: 177–178° C.

Example 47

3-Benzyloxy-N-[2-[[(octylamino)carbonylamino]sulfonyl]phenyl]benzamide

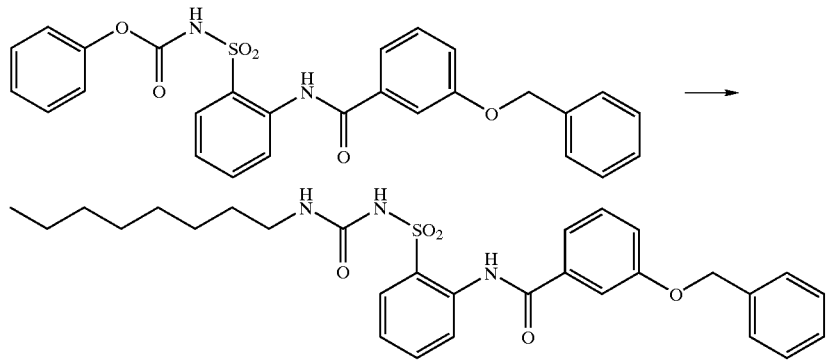

A benzene (10 ml) solution containing 200 mg (0.40 mmol) of 3-benzyloxy-N-[2-[(phenyloxycarbonylamino)sufonyl]phenyl]benzamide produced in Example 45 and 0.15 mol (0.88 mmol) of octylamine was heated under reflux for 2 hours. The reaction mixture was dissolved in ethyl acetate, washed with water, a potassium hydrgensulfate aqueous solution and saturated brine in that order and dried over anhydrous sodium sulfate, and then the solvent was evaporated under a reduced pressure. The resulting residue was purified by a silica gel chromatography to obtain 210 mg (yield: 98.0%) of the title compound.

NMR (CDCl$_3$) δ: 0.88 (3H, t, J=7Hz), 1.10–1.40 (12H, m), 3.00 (2H, dt, J=7, 7Hz), 5.14 (2H, s), 6.15 (1H, br-s), 7.17 (1H, ddd, J=8Hz, 2Hz, 1Hz), 7.23 (1H, ddd, J=8Hz, 8Hz, 1Hz), 7.31–7.42 (5H, m), 7.46 (2H, d, J=8Hz), 7.53 (1H, d, J=8Hz), 7.62–7.70 (2H, m), 7.86 (1H, dd, J=8Hz, 2Hz), 8.07 (1H, br-s), 8.71 (1H, d, J=8Hz), 10.11 (1H, s)

IR (v, cm$^{-1}$, KBr): 1702, 1650, 1580, 1540, 1450, 1356, 1332, 1164 FAB-MS (neg: m/z, %): 536 ([M-H]+63), 368 (70), 272 (100)

Melting point: 124–125° C.

Pharmacological Test Example 1

Measurement of ACC inhibition activity
1. Purification of ACC

After 2 days of fasting, a male SD rat of 12 weeks of age was allowed to feed on a high sucrose feed (67% sucrose, 17.1% casein, 9.8% cellulose, 5% sodium chloride, 0.1% choline chloride and 1% vitamins) for 2 days and then subjected to decapitation and bloodletting under ether anesthesia to quickly take out the liver. The thus obtained liver was sliced in an ice-cooled buffer A (225 mM mannitol, 75 mM sucrose, 10 mM Tris/HCl (pH 7.5), 0.05 mM EDTA-2Na, 5 mM potassium citrate, 2.5 mM MnCl$_2$, 10 mg/l aprotinin, 10 mg/l leupeptin and 10 mg/l antitrypsin) and then, after removal of moisture, adjusted to 5 ml/g by adding the buffer A and homogenized for 4 minutes using Polytron homogenizer. This was centrifuged for 10 minutes at 1,000 g and then the resulting supernatant was subjected to 10 minutes of high speed centrifugation at 17,000 g.

Ammonium sulfate was added to the thus obtained supernatant to a final concentration of 35%, and the mixture was stirred for 45 minutes and then subjected to 10 minutes of high speed centrifugation at 17,000 g. The thus obtained precipitate was mixed with 100 ml of a buffer B (100 mM Tris/HCl (pH 7.5 ), 0.5 M NaCl, 1 mM EDTA-2Na, 0.1 mM DTT, 10% glycerol, 10 mg/l aprotinin, 10 mg/l leupeptin and 10 mg/l antitrypsin) and subjected to 20 minutes of ultracentrifugation at 40,000, and the resulting supernatant was dialyzed overnight against 150 volumes of a buffer C (100 mM Tris/HCl (pH 7.5), 0.5 M NaCl, 1 mM EDTA-2Na, 0.1 mM DTT and 10% glycerol) and then filtered through a 5 μm filter. The filtrate was applied to a biotin affinity column, washed with the buffer B and then eluted with the buffer B supplemented with 5 mM biotin.

2. Measurement of ACC inhibition activity

Each of the compounds produced in the Examples was dissolved in DMSO, and the solution was put into a glass vial, mixed with 250 μl of an ACC-containing reagent 1 (40 mM Tris/HCl (pH 7.5), 40 mM MgCl$_2$, 40 mM sodium citrate, 2 mM DTT and 100 μg/ml fatty acid-free BSA), incubated at 37° C. for 30 minutes in a thermostatic chamber, cooled with ice, mixed with 250 μl of a reagent 2 (40 mM Tris/HCl (pH 7.5), 2 mM DTT, 8 mM ATP and 0.5 mM acetyl-CoA) containing 74 kBq of NaH$^{14}$CO$_3$, again incubated at 37° C. for 10 minutes in a thermostatic chamber and then mixed with 0.1 ml of 1 N HCl to terminate the reaction. After complete removal of moisture in the glass vial under a reduced pressure, an emulsified scintillator (Cleasol I) was added to the glass vial, and the $^{14}$C radioactivity was measured using a liquid scintillation counter. The inhibition activity of each compound (5.6×10$^{-6}$ mol) was calculated based on the following formula. Inhibition activity ratio (%)=(1−radioactivity when a drug to be tested is added/radioactivity when the drug to be rested is not added)×100

The results are shown in Table 1.

Pharmacological Test 2

Measurement of intracellular fatty acid synthesis inhibition activity (FA biosynthesis inhibition activity)

Each of the compounds produced in the Examples was dissolved in DMSO and added to an experimental culture medium (DMEM; 0.05 μg/ml insulin, 0.1 mg/ml glucose and 18.5 kBg/ml [$^{14}$C]-glucose). The HepG2 cells were adjusted to a density of 0.75×10$^6$ cells/ml, inoculated into a 12 well plate in an amount of 1 ml/well and cultured overnight at 37° C. in an atmosphere of 5% CO$_2$ (culture medium: DMEM, 4.5 g/ml glucose and 10% FBS), and the resulting cells were washed twice with PBS(−) buffer, mixed with the experimental culture medium in an amount of 0.5 ml/well and then cultured at 37° C. for 3 hours in an atmosphere of 5% CO$_2$. After the culturing, the cells were washed twice with ice-cooled PBS(−) buffer and peeled off, and lipids were extracted from the resulting cells with a lipid extraction solution (chloroform:methanol=2:1). The extract was mixed with 2.5 ml of ethanol and 0.1 ml of 33% potassium hydroxide and incubated at 70° C. for 1 hour. Lipids were again extracted from the reaction mixture, and the extract was applied to a silica gel thin layer plate. This was developed with a developing solution (hexane:diethyl ether:acetic acid=80:20:1) and then the fatty acid iodine-coloring part was collected to measure its radioactivity using a liquid scintillation counter. The inhibition activity % (3.0×10$^{-5}$ M) of each compound was calculated. The results are shown in Table 1.

TABLE 1

| Example No. | Compound Name | ACC inhibition activity (%) (5.6 × 10$^{-6}$ M) | FA synthesis inhibition (%) (3.0 × 10$^{-5}$ M) |
|---|---|---|---|
| 2 | 3-benzyloxy-N-[2-(3-benzyloxybenzamido) benzenesulfonyl]benzamide | 60.7 | 43.9 |
| 9 | N-[2-(3-benzyloxybenzamido) benzenesulfonyl]decanamide | 65.0 | 66.6 |
| 13 | N-[2-[3-(4-t-butylbenzyloxy)benzamido] benzenesulfonyl]cinnamamide | 79.5 | 36.1 |
| 15 | N-[2-(3-benzyloxybenzamido) benzenesulfonyl]linolamide | 84.8 | 30.6 |
| 16 | N-[2-(3-benzyloxy-4-nitrobenzamido) benzenesulfonyl]decanamide | 79.9 | 94.3 |
| 19 | N-[2-[3-(4-chlorobenzyloxy) benzamido]benzenesulfonyl]decanamide | 83.3 | 90.5 |
| 22 | N-[2-[3-(4-nitrobenzyloxy) benzamide]benzenesulfonyl]decanamide | 88.4 | 95.2 |
| 25 | N-[2-[3-(4-methoxybenzyloxy) benzamido]benzenesulfonyl]decanamide | 81.6 | 92.0 |
| 28 | N-[2-(3-cyclohexylmethoxybenzamido) benzenesulfonyl]decanamide | 89.4 | 84.6 |
| 30 | N-[2-[3-(4-t-butylbenzyloxy) benzamido]benzenesulfonyl]hexanamide | 53.2 | 87.1 |
| 31 | N-[2-[3-(4-t-butylbenzyloxy) benzamido]benzenesulfonyl]decanamide | 67.6 | 66.4 |
| 33 | N-[2-[3-(4-trifluoromethylbenzyloxy) benzamido]benzenesulfonyl]hexanamide | 52.3 | 97.5 |
| 34 | N-[2-[3-(4-trifluoromethylbenzyloxy) benzamido]benzenesulfonyl]decanamide | 81.3 | 87.7 |
| 37 | N-[2-(3-heptyloxybenzamido) benzenesulfonyl]decanamide | 83.6 | 64.3 |

TABLE 1-continued

| Example No. | Compound Name | ACC inhibition activity (%) (5.6 × 10⁻⁶ M) | FA synthesis inhibition (%) (3.0 × 10⁻⁵ M) |
|---|---|---|---|
| 39 | N-[2-(4-phenylethynylbenzamido)benzenesulfonyl]hexanamide | 61.3 | 92.2 |
| 40 | N-[2-(4-phenylethynylbenzamido)benzenesulfonyl]decanamide | 76.0 | 57.4 |
| 43 | trans-N-[2-(4-phenylethynylbenzamido)benzenesulfonyl]-2,4-hexadienamide | 54.3 | 92.3 |

Thus, as has been described in the foregoing, the invention provides a novel acylsulfonamide derivative represented by the general formula (I), which can be used as an ACC activity inhibitor effective for the treatment of visceral fat syndrome that becomes the risk-factor of diseases of adult people such as myocardial infarction, cerebral infarction and diabetes, so that its effects in terms of medical treatment are considerable.

This application is based on a Japanese patent application No. 9-277943 filed on Sep. 26, 1997 and a Japanese patent application No. 10-270728 filed Sep. 25, 1998, both incorporated herein by reference.

What is claimed is:

1. An acylsulfonamide derivative represented by a general formula (I)

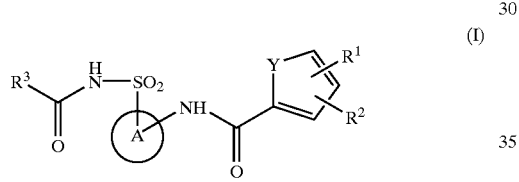

(I)

wherein
R¹ represents a substituted or unsubstituted $C_1$–$C_{12}$ alkyl group, a substituted or unsubstituted $C_2$–$C_{12}$ alkenyl group, a substituted or unsubstituted $C_2$–$C_{12}$ alkynyl group or a substituted or unsubstituted $C_1$–$C_{12}$ alkoxy group, R² represents a hydrogen atom, a hydroxyl group, a mercapto group, a substituted or unsubstituted $C_1$–$C_6$ alkoxy group, a substituted or unsubstituted $C_1$–$C_6$ alkylthio group, a nitro group, a halogen atom, a trichloromethyl group, a trifluoromethyl group or a cyano group, R³ represents a substituted or unsubstituted $C_1$–$C_{20}$ alkyl group, a substitute or unsubstituted $C_2$–$C_{20}$ alkenyl group, a substituted or unsubstituted $C_2$–$C_{20}$ alkynyl group, a substituted or unsubstituted aromatic hydrocarbon group, a substituted or unsubstituted aromatic heterocyclic group, a substituted amino group, a substituted or unsubstituted $C_1$–$C_{20}$ alkoxy group, a substituted or unsubstituted $C_2$–$C_{20}$ alkenyloxy group, a substituted or unsubstituted $C_2$–$C_{20}$ alkynyloxy group or a group represented by R⁴O— (wherein R⁴ represents a substituted or unsubstituted aromatic hydrocarbon group or a substituted or unsubstituted aromatic heterocyclic group), Y is a group represented by —CH=CH—, ring A is an aromatic hydrocarbon group, to which the acylsulfonamide side chain and the amide side chain are bonded at the 1,2-positions.

2. An acylsulfonamide derivative according to claim 1, wherein R¹ is a $C_1$–$C_4$ alkyl group having a substituted or unsubstituted aromatic hydrocarbon group or a substituted or unsubstituted aromatic heterocyclic group as a substituent, a $C_2$–$C_4$ alkenyl group having a substituted or unsubstituted aromatic hydrocarbon group or a substituted or unsubstituted aromatic heterocyclic group as a substituent, a $C_2$–$C_4$ alkenyl group having a substituted or unsubstituted aromatic hydrocarbon group or a substituted or unsubstituted aromatic heterocyclic group as a substituent or a $C_1$–$C_4$ alkoxy group having a substituted or unsubstituted aromatic hydrocarbon group or a substituted or unsubstituted aromatic heterocyclic group as a substituent.

3. An acylsulfonamide derivative according to claim 1, wherein R¹ is an unsubstituted $C_5$–$C_{12}$ alkyl group, an unsubstituted $C_5$–$C_{12}$ alkenyl group, an unsubstituted $C_5$–$C_{12}$ alkynyl group or an unsubstituted $C_5$–$C_{12}$ alkoxy group.

4. An acylsulfonamide derivative according to claim 1, wherein:
R¹ represents:
(a) a $C_1$–$C_{12}$ alkyl group, which may be substituted with one or more substituents selected from the group consisting of halogen atom, nitro group, amino group, cyano group, hydroxyl group, alkoxy group, thiol group, trichloromethyl group, trifluoromethyl group, phenyl group, naphthyl group, thienyl group, furyl group, and pyridyl group, and wherein said phenyl group, naphthyl group, thienyl group, furyl group, and pyridyl group may be substituted with one or more substituents selected from the group consisting of halogen atom, alkyl group, alkoxy group, nitro group, amino group, cyano group, hydroxyl group, and thiol group;

(b) a $C_2$–$C_{12}$ alkenyl group, which may be substituted with one or more substituents selected from the group consisting of halogen atom, nitro group, amino group, cyano group, hydroxyl group, alkoxy group, thiol group, trichloromethyl group, trifluoromethyl group, phenyl group, naphthyl group, thienyl group, furyl group, and pyridyl group, and wherein said phenyl group naphthyl group, thienyl group, furyl group, and pyridyl group may be substituted with one or more substituents selected from the group consisting of halogen atom, alkyl group, alkoxy group, nitro group, amino group, cyano group, hydroxyl group, and thiol group;

(c) a $C_2$–$C_{12}$ alkynyl group, which may be substituted with one or more substituents selected from the group consisting of halogen atom, nitro group, amino group, cyano group, hydroxyl group, alkoxy group, thiol group, trichloromethyl group, trifluoromethyl group, phenyl group, naphthyl group, thienyl group, furyl group, and pyridyl group, and wherein said phenyl group, naphthyl group, thienyl group, furyl group, and pyridyl group may be substituted with one or more substituents selected from the group consisting of halogen atom, alkyl group, alkoxy group, nitro group, amino group, cyano group, hydroxyl group, and thiol group; or (d) a $C_1$–$C_{12}$ alkoxy group, which may be substituted with one or more substituents selected from the group consisting of halogen atom, nitro group, amino group, cyano group, hydroxyl group, alkoxy group, thiol group, trichloromethyl group, trifluoromethyl group, phenyl group, naphthyl group, thienyl group, furyl group, and pyridyl group, and wherein said phenyl group, naphthyl group, thienyl group, furyl group, and pyridyl group may be substituted with one or more substituents selected from the group consisting of halogen atom, alkyl group, alkoxy group, nitro group, amino group, cyano group, hydroxyl group, and thiol group;

$R^2$ represents:
  (a) a hydrogen atom;
  (b) a hydroxyl group;
  (c) a mercapto group;
  (d) a $C_1$–$C_6$ alkoxy group, which may be substituted with one or more substituents selected from the group consisting of halogen atom, nitro group, amino group, cyano group, hydroxyl group, alkoxy group, thiol group, trichloromethyl group, trifluoromethyl group, phenyl group, naphthyl group, thienyl group, furyl group, and pyridyl group, and wherein said phenyl group, naphthyl group, thienyl group, furyl group, and pyridyl group may be substituted with one or more substituents selected from the group consisting of halogen atom, alkyl group, alkoxy group, nitro group, amino group, cyano group, hydroxyl group, and thiol group;
  (e) a $C_1$–$C_6$ alkylthio group, which may be substituted with one or more substituents selected from the group consisting of halogen atom, nitro group, amino group, cyano group, hydroxyl group, alkoxy group, thiol group, trichloromethyl group, trifluoromethyl group, phenyl group, naphthyl group, thienyl group, furyl group, and pyridyl group, and wherein said phenyl group, naphthyl group, thienyl group, furyl group, and pyridyl group may be substituted with one or more substituents selected from the group consisting of halogen atom, alkyl group, alkoxy group, nitro group, amino group, cyano group, hydroxyl group, and thiol group;
  (f) a nitro group;
  (g) a halogen atom;
  (h) a trichloromethyl group;
  (i) a trifluoromethyl group; or
  (j) a cyano group;

$R^3$ represents:
  (a) a $C_1$–$C_{20}$ alkyl group, which may be substituted with one or more substituents selected from the group consisting of halogen atom, nitro group, amino group, cyano group, hydroxyl group, alkoxy group, thiol group, trichloromethyl group, trifluoromethyl group, phenyl group, naphthyl group, thienyl group, furyl group, and pyridyl group, and wherein said phenyl group, naphthyl group, thienyl group, furyl group, and pyridyl group may be substituted with one or more substituents selected from the group consisting of halogen atom, alkyl group, alkoxy group, nitro group, amino group, cyano group, hydroxyl group, and thiol group;
  (b) a $C_2$–$C_{20}$ alkenyl group, which may be substituted with one or more substituents selected from the group consisting of halogen atom, nitro group, amino group, cyano group, hydroxyl group, alkoxy group, thiol group, trichloromethyl group, trifluoromethyl group, phenyl group, naphthyl group, thienyl group, furyl group, and pyridyl group, and wherein said phenyl group, naphthyl group, thienyl group, furyl group, and pyridyl group may be substituted with one or more substituents selected from the group consisting of halogen atom, alkyl group, alkoxy group, nitro group, amino group, cyano group, hydroxyl group, and thiol group;
  (c) a $C_2$–$C_{20}$ alkynyl group, which may be substituted with one or more substituents selected from the group consisting of halogen atom, nitro group, amino group, cyano group, hydroxyl group, alkoxy group, thiol group, trichloromethyl group, trifluoromethyl group, phenyl group, naphthyl group, thienyl group, furyl group, and pyridyl group, and wherein said phenyl group, naphthyl group, thienyl group, furyl group, and pyridyl group may be substituted with one or more substituents selected from the group consisting of halogen atom, alkyl group, alkoxy group, nitro group, amino group, cyano group, hydroxyl group, and thiol group;
  (d) an aromatic hydrocarbon group, which may be substituted with one or more substituents selected from the group consisting of methyl, methoxy, nitro, chloro, bromo, iodo, fluoro, amino, hydroxy, and —SH;
  (e) an aromatic heterocyclic group;
  (f) an amino group, which may be substituted with one or two substituents selected from the group consisting of substituted or unsubstituted $C_1$–$C_{20}$ alkyl groups, substituted or unsubstituted $C_2$–$C_{20}$ alkenyl groups, substituted or unsubstituted $C_2$–$C_{20}$ alkynyl groups, substituted or unsubstituted aromatic hydrocarbon groups, and aromatic heterocyclic groups, and wherein said alkyl groups together with the binding nitrogen atom may form a five-to seven-membered saturated heterocyclic ring which may contain nitrogen atom, oxygen atom or sulfur atom, and wherein the substituents for said groups bonded to said nitrogen are the same as described for said $C_1$–$C_{12}$ alkyl group in the definition of $R^1$ above;
  (g) a $C_1$–$C_{20}$ alkoxy group, which may be substituted with one or more substituents selected from the group consisting of halogen atom, nitro group, amino group, cyano group, hydroxyl group, alkoxy group, thiol group, trichloromethyl group, trifluoromethyl group, phenyl group, naphthyl group, thienyl group, furyl group, and pyridyl group, and wherein said phenyl group, naphthyl group, thienyl group, furyl group, and pyridyl group may be substituted with one or more substituents selected from the group consisting of halogen atom, alkyl group, alkoxy group, nitro group, amino group, cyano group, hydroxyl group, and thiol group;
  (h) a $C_2$–$C_{20}$ alkenyloxy group, which may be substituted with one or more substituents selected from the group consisting of halogen atom, nitro group, amino group, cyano group, hydroxyl group, alkoxy group, thiol group, trichloromethyl group, trifluoromethyl group, phenyl group, naphthyl group, thienyl group, furyl group, and pyridyl group, and wherein said phenyl group, naphthyl group, thienyl group, furyl group, and pyridyl group may ne substituted with one or more substituents selected from the group consisting of halogen atom, alkyl group, alkoxy group, nitro group, amino group, cyano group, hydroxyl group, and thiol group;
  (i) a substituted or unsubstituted $C_2$–$C_{20}$ alkynyloxy group;one or more substituents selected from the group consisting of halogen atom, nitro group, amino group, cyano group, hydroxyl group, alkoxy group, thiol group, trichloromethyl group, trifluo romethyl group, phenyl group, naphthyl group, thienyl group, furyl group, and pyridyl group, and wherein said phenyl group, naphthyl group, thienyl group, furyl group, and pyridyl group may be substituted with one or more substituents selected from the group consisting of halogen atom, alkyl group, alkoxy group, nitro group, amino group, cyano group, hydroxyl group, and thiol group; or (j) a group represented by $R^4O$— (wherein $R^4$ represents a substituted or unsubstituted aromatic hydrocarbon group or a substituted or unsubstituted aromatic heterocyclic group);

Y is a group represented by —CH=CH—; and ring A represents an aromatic hydrocarbon group, which may be substituted with one or more substituents selected from the group consisting of methyl, methoxy, nitro, chloro, bromo, iodo, fluoro, amino, hydroxy, and —SH.

5. A pharmaceutical composition, which comprises any one of the acylsulfonamide derivatives of claims 1, 2, 3, or 4, or a pharmacologically acceptable salt thereof, as an active ingredient.

* * * * *